United States Patent
Dharmadhikari et al.

(10) Patent No.: US 9,610,269 B2
(45) Date of Patent: Apr. 4, 2017

(54) METHOD OF TREATING A DISEASE CONDITION SUSCEPTIBLE TO BACLOFEN THERAPY

(71) Applicant: SUN PHARMA ADVANCED RESEARCH COMPANY LTD., Mumbai (IN)

(72) Inventors: Nitin Bhalachandra Dharmadhikari, Mumbai (IN); Yashoraj Rupsinh Zala, Mumbai (IN)

(73) Assignee: SUN PHARMA ADVANCED RESEARCH COMPANY LTD., Mumbai (IN)

( * ) Notice: Subject to any disclaimer, the term of this patent is extended or adjusted under 35 U.S.C. 154(b) by 151 days.

(21) Appl. No.: 14/107,245

(22) Filed: Dec. 16, 2013

(65) Prior Publication Data

US 2014/0105973 A1 Apr. 17, 2014

Related U.S. Application Data

(63) Continuation of application No. 13/029,722, filed on Feb. 17, 2011, now abandoned.

(30) Foreign Application Priority Data

Feb. 17, 2010 (IN) .......................... 429/MUM/2010

(51) Int. Cl.
| | | |
|---|---|---|
| *A61K 31/197* | (2006.01) | |
| *A61K 9/00* | (2006.01) | |
| *A61K 9/24* | (2006.01) | |
| *A61K 9/48* | (2006.01) | |
| *A61K 9/50* | (2006.01) | |

(52) U.S. Cl.
CPC ............ *A61K 31/197* (2013.01); *A61K 9/006* (2013.01); *A61K 9/0065* (2013.01); *A61K 9/209* (2013.01); *A61K 9/4866* (2013.01); *A61K 9/4891* (2013.01); *A61K 9/5047* (2013.01)

(58) Field of Classification Search
USPC ....................................................... 514/567
See application file for complete search history.

(56) References Cited

U.S. PATENT DOCUMENTS

| | | |
|---|---|---|
| 6,261,601 B1 | 7/2001 | Talwar et al. |
| 2002/0119192 A1 | 8/2002 | Vishwanathan et al. |
| 2003/0031711 A1 | 2/2003 | Fara et al. |
| 2007/0265343 A1 | 11/2007 | Dharmadhikari et al. |
| 2008/0206332 A1 | 8/2008 | Kidney et al. |

FOREIGN PATENT DOCUMENTS

| | | |
|---|---|---|
| WO | 00/25821 A1 | 5/2000 |
| WO | 2005/101983 A2 | 11/2005 |
| WO | 2007/089934 A2 | 8/2007 |

OTHER PUBLICATIONS

Alkermes, Inc. completed clinical trial No. NCT00802035, ALK29-002: A Study of Baclofen Formulations in Healthy Adults, 2008.
Guilleminault et al., "Effect of Baclofen on Sleep-Related Periodic Leg Movements." Ann Neurol 1984:15;234-239.
Sampat, Nitin G., "Once daily baclofen sustained release or gastro-retentive system are acceptable alternatives to thrice daily baclofen immediate release at same daily dosage in patients", Neuro. India, 2009, 57(3), 295-299.

*Primary Examiner* — Walter Webb
(74) *Attorney, Agent, or Firm* — Sughrue Mion, PLLC

(57) ABSTRACT

The present invention discloses a method of treating a disease condition susceptible to baclofen therapy, said method comprising orally administering once-a-day in the evening a controlled release drug delivery system comprising baclofen or its pharmaceutically acceptable salt or its derivatives and pharmaceutically acceptable excipients.

12 Claims, 4 Drawing Sheets

METHOD OF TREATING A DISEASE CONDITION SUSCEPTIBLE TO BACLOFEN THERAPY

This is a Continuation of application Ser. No. 13/029,722 filed Feb. 17, 2011, claiming priority based on Indian Patent Application No. 429/MUM/2010 filed Feb. 17, 2010, the contents of all of which are incorporated herein by reference in their entirety.

FIELD OF INVENTION

The present invention relates to an effective method of treating a disease condition susceptible to baclofen therapy, said method comprising administering a controlled release drug delivery system of baclofen or its pharmaceutically acceptable salts or its derivatives.

The present invention also relates to an effective method of treating disease conditions susceptible to baclofen therapy, said method comprising administering a controlled release drug delivery system of baclofen or its pharmaceutically acceptable salts or its derivatives and to the use of baclofen for such treatment.

BACKGROUND OF THE INVENTION

U.S. Pat. No. 3,471,548 disclosed 4-amino-3-(p-chlorophenyl) butyric acid). 4-amino-3-(p-chlorophenyl) butyric acid) designates the R-isomers, the S-isomer and mixtures of R and S isomers including the racemate. Baclofen is indicated in many disease conditions such as for alleviating signs and symptoms of spasticity resulting from multiple sclerosis, particularly for the relief of flexor spasms and concomitant pain, clonus and muscular rigidity; in treatment of gastroparesis, non ulcer dydpepsia, gastroesophageal reflux diseases, for the treatment of depression or other psychological conditions, such as posttraumatic stress disorders, alcohol related disorders such as alcohol dependence is a chronic disorder that results from a variety of genetic, physiological and environmental factors, for promoting smoking cessation; for reducing addiction liability of narcotic agents; in the treatment of emesis; as an anti-tussive for the treatment of cough; in treating neuropathic pain and in treating musculoskeletal pain.

Clinical studies wherein baclofen is used for the treatment of spasticity have indicated that its major site of action is the spinal cord. Spasticity is one of the components of the upper motor neuron (UHM) syndrome but should not be considered in isolation when it comes to management strategies. Baclofen is used as a muscle relaxant and an anti-spastic agent for a variety of neurological disorders. It is a GABA-B receptor agonist that depresses the monosynaptic and polysynaptic excitation of mononeurons and interneurons. Currently, the most commonly used dosage form of racemic baclofen is the immediate release (IR) tablet (10-20 mg) to be administered three times a day. A serum concentration of 80 ng/ml or more is considered an effective concentration.

There is a wide inter-subject variation in the absorption and elimination of baclofen, but on an average it is rapidly and extensively absorbed after oral administration. Plasma elimination half-life of baclofen is approximately 3.5 hours (range 2 to 6 hours). Baclofen is excreted mainly by the kidneys in unchanged form although 15% is metabolized in the liver. Conventional baclofen therapy involves administration of 10 mg or 20 mg immediate release tablets three times a day. The dose ranges from 30 mg to 100 mg/day in divided doses. Baclofen is also available in the USA for chronic use as an injection to be administered by the intrathecal route in single bolus test doses (via spinal catheter or lumbar puncture), and as implantable pumps approved by the Food and Drug Administration specifically for the administration of baclofen injection into the intrathecal space.

Frequent administration of immediate release baclofen tablets leads to fluctuations in plasma concentration producing peaks and troughs. Peaks in plasma concentration are associated with side effects, such as drowsiness (sedation), dizziness and muscle weakness and troughs cause inadequate control of muscle spasm. Side effects, like drowsiness and muscle weakness, are considered as major deterrents to the prescribers for up titration of the dosage for optimization of therapy. It is a matter of general concern, with conventional baclofen therapy, that the medication has to be administered frequently. Medication noncompliance among patients with medical illnesses has been reported to range from 15% to 85%. Although many factors are associated with medication non-compliance, it is thought that physicians can help promote compliance by prescribing medications that require a minimal number of doses.

A once-a-day or twice-a-day (b.i.d.) dosage formulation with the same therapeutic effectiveness as the conventional baclofen therapy could vastly improve patients' compliance with treatment. These will also improve the outcome of therapy, as a greater number of patients will adhere to treatment plan.

Although a single daily administration of the full daily dose (referred to as "high dose" to signify the higher amount of baclofen in a single sustained release tablet compared to that in one immediate release tablet even though the total daily dose remains the same) would be convenient however, the problem was that when baclofen was given in single high daily doses as sustained or controlled release preparation the bioavailability was reduced. This problem was studied by Merino et al (*Proc. Eur. Congr. Biopharm. Pharmacokinet.*, $3^{rd}$ (1987), 2, 564-73) and *Biopharmaceutics and Drug Disposition* (1989), 10(3), 279-97). The authors made significant conclusions about absorption of baclofen:

1. The lipophilicity of the drug at the actual pH values is negligible and therefore passive absorption mechanism for baclofen will be virtually inoperative and aqueous pore diffusion will be limited in view of the molecular weight of the drug. This limits the mechanisms by which baclofen can be absorbed to active or carrier mediated transport.
2. The absorption from the small intestine could occur due to the presence of a carrier mediated transport mechanism
3. No absorption could occur in the colon because of the absence of a carrier mediated transport mechanism.
4. Absorption of baclofen occurs by specialized transport mechanism which is saturable at higher concentrations and thus the use of high doses of baclofen is not recommended.
5. It can therefore be predicted that if controlled release formulations of baclofen are to be considered, they should be designed so that they would release most of the drug before reaching the illeo-caecal junction, i.e within no more than 8 hours.

Further, it is known that gastric motility presents a significant resistance to preventing the passage of a dosage form into the colon for more than 8 hours. This resistance is due to the strong propulsive movements of the gut, particularly the occurrence of a periodic housekeeper wave that would sweep any physical object from the stomach into the intestine. (see $T_{max}$ in FIG. 1 and Table 7 when the systems were given in the fed state in the morning). The reasons for such shortfalls are suspected to lie in the nature of gastric motility and gastric emptying (See page 145 of E. A. Klausner et al, Journal of Controlled release 90 (2003), 143-162). The motor activity in the fed state is induced 5-10 min after ingestion of a meal and persists as long as food remains in the stomach, which may be from as short as about 2 hrs to as long as about 6 hrs, typically 3-4 hrs. In this period the contraction are of intermediate amplitudes. At the end of the fed phase, the motility pattern changes and goes into a fasted mode characterized by four periods of peristaltic activity over a 2 hr period. The aim of this activity is to clear the stomach and the small intestine of indigestible debris. It has four phases of which the third phase is known as the housekeeper phase characterized by very high amplitude contractions lasting for 5-15 minutes. Anything in the stomach is expected to be cleared due to these strong contractions or otherwise cause the problems of blocking of the pyloric sphincter or accumulation of the object in the stomach after it is repeatedly ingested by the human subject. It is also not possible to use a dosage form that would resist such housekeeper waves because it will be totally unacceptable for safety reasons to allow the accumulation of the residual dosage form in the stomach.

Nevertheless with the doubts whether a controlled drug delivery systems would provide adequate bioavailability, the present inventors proceeded to design and test a once-a-day controlled drug delivery system for baclofen to investigate possibilities of overcoming the drawbacks of poor absorption of baclofen in the lower parts of the intestine and obtain adequate bioavailability and a plasma profile with lower fluctuation in plasma levels. Two of such controlled drug delivery systems were disclosed in the pending patent applications US 20040180088 and US 20080107732. The bioavailability of baclofen from these controlled drug delivery systems containing 30 mg of baclofen was compared to the bioavailability of baclofen in the fed state (normal diet) from immediate release tablets (15 mg tablets given twice a day) in a comparative, open label, randomized two-way cross-over study in twelve healthy volunteers. It was found that the relative bioavailability of baclofen from the gastric retention controlled drug delivery system was 80% of the bioavailability from the immediate release tablets. These results were achieved by improving the design of prior known controlled drug delivery systems by incorporating features that cause the systems to expand in the gastric fluids and consequently be retained over longer periods in the stomach. However, this alone was not sufficient and an additional design feature in these systems was that they released a fraction of the drug in a more absorbable immediate release form that contributed to baclofen levels only for the initial duration of the 24 hr dosing nevertheless it obtained 24 hrs desired plasma levels by combining the more absorbable form with the slow release form which is criticized in the prior art as being "poorly absorbable".

The inventors proceeded further to investigate whether this extent of absorption of baclofen from these once-a-day controlled drug delivery systems would also be obtained in patients suffering from spasticity and whether it was adequate to provide the desired efficacy over the duration of a day. It was surprisingly found that while the controlled release drug delivery demonstrated an efficacy equivalent to the immediate release baclofen tablets it also showed lower levels of sedation. Thus, a method of alleviating signs and symptoms of spasticity in human patient using once a day therapy was discovered for the first time. The method provided the benefit of reduced levels of sedation as compared to therapy with immediate release tablets and was claimed in US 20070265343 (European patent application EP 1849 462 A2 the contents of which are incorporated herein by reference). The EP 1849462 A2 claims a method of alleviating signs and symptoms of spasticity in human patient comprising orally administering to said human patients once in a day a controlled drug delivery system comprising an effective daily dose of baclofen or its pharmaceutically acceptable salt wherein said method is associated with reduced level of sedation in said patients as compared to conventional baclofen therapy with immediate release tablets administered three times a day on the same total daily dose. It further related to a method wherein the daily dose of baclofen or its pharmaceutically acceptable salt ranges from about 15 mg to about 80 mg. Particularly the method was useful when the daily dose of racemic baclofen was 30 mg or 45 mgs. The finding invention was surprising because instead of continuous treatment, in the sense of multiple daily dosing, with baclofen for patients suffering from spasticity which leads to the side effect of sedation, using an intermittent, in the sense of once a day, dosing amounting to the same overall daily dosage not only allows effective treatment of the underlying condition of spasticity but also reduces or eliminates the side effect of sedation. This was particularly surprising since the administration of a once a day formulation lead to higher plasma levels than the equivalent multiple dosing regimen and thus would ordinarily be expected to be associated with increased sedation as a side effect. Without wishing to be bound by theory, it is believed that the unexpected success of the formulations used arose as a consequence that they are retained in the stomach for longer than other systems. It was therefore an important benefit that the scope of industrial applicability and marketability of baclofen was increased because it could be used in a wider range of circumstances than previously possible when the risk of sedation might have precluded its use. Also, the invention could be particularly useful for treating patients who have a predisposition to suffering sedation as a side effect.

SUMMARY OF THE INVENTION

It has surprisingly been found that when controlled release drug delivery system comprising baclofen or its pharmaceutically acceptable salt or its derivative was administered to human subjects in the evening in the fed state, the maximum plasma concentration of baclofen ($C_{max}$) achieved after administration of the system in evening was sustained over a longer duration (see FIG. 1 and FIG. 3) than compared to that after administration of the system in the morning in the fed state. Surprisingly when the system was administered in the evening, it was observed that the duration over which absorption of baclofen occurred was prolonged and higher plasma levels were maintained during the latter half of the dosing period as compared to those obtained by morning dosing. Evening dosing thus can provide an optimum maintenance of relief from the systems of the disease condition by maintaining baclofen levels at higher therapeutic effective plasma concentrations even in the latter half of the dosing period.

The improved method of the present invention is useful for treating disease conditions such as spasticity, gastroparesis, gastro-esophageal reflux diseases, for the treatment of depression or other psychological conditions, alcohol related disorders such as alcohol dependence, smoking cessation, addiction liability of narcotic agents, emesis, cough, hiccoughs, neuropathic pain and musculoskeletal pain.

OBJECTS OF THE INVENTION

In various aspects and embodiments, the present invention seeks to provide an improved method of treating a disease condition susceptible to baclofen therapy.

DESCRIPTION OF DRAWINGS AND FIGURES

The patent or application file contains at least one drawing executed in color. Copies of this patent or patent application publication with color drawing(s) will be provided by the Office upon request and payment of the necessary fee.

Many aspects of the invention can be better understood with reference to the following figures. The figures only represent one of the embodiments of the present invention. The embodiments are meant only for the purpose of illustration of the present invention. The components in the drawings are not necessarily to scale, emphasis instead being placed upon clearly illustrating the principles of the present invention.

Figure 3:
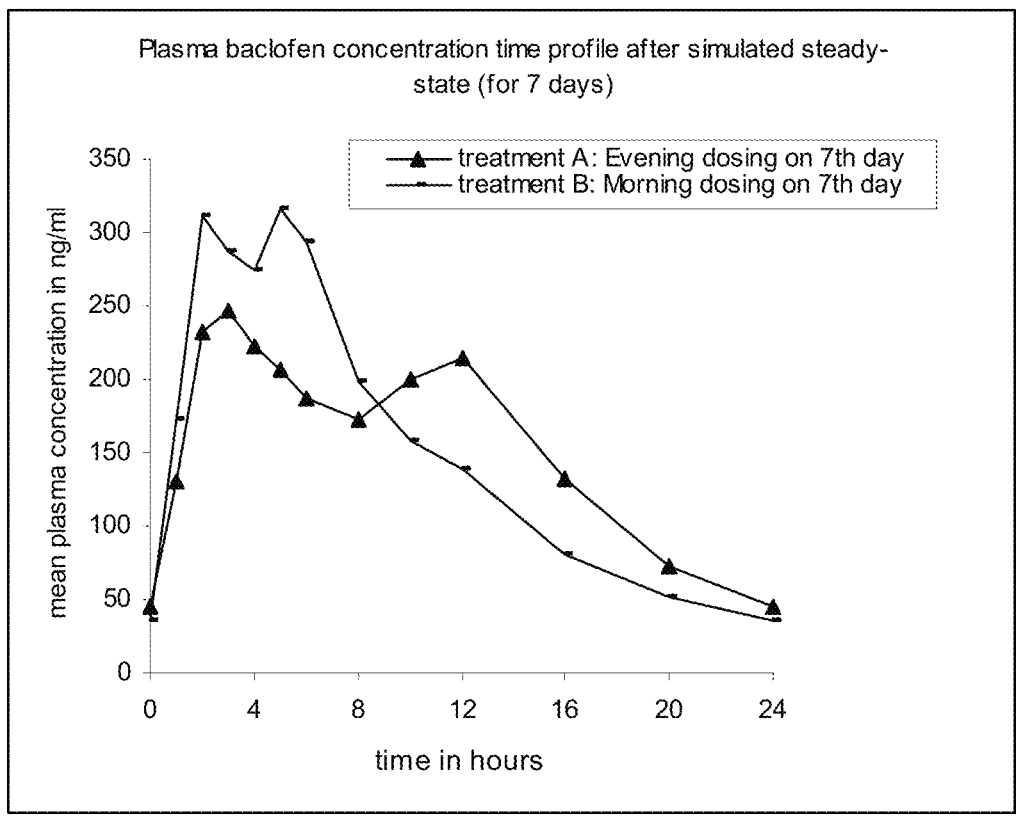

FIG. 3 depicts the graph of the mean plasma baclofen concentration time profiles at steady-state for baclofen 60 mg controlled release drug delivery system in the form of capsule administered by healthy human volunteers under fed (normal meal) condition in evening once daily for 7 days according to the present invention; and baclofen 60 mg controlled release drug delivery system in the form of capsule administered healthy human volunteers under fed (normal meal) condition in morning.

Figure 4:
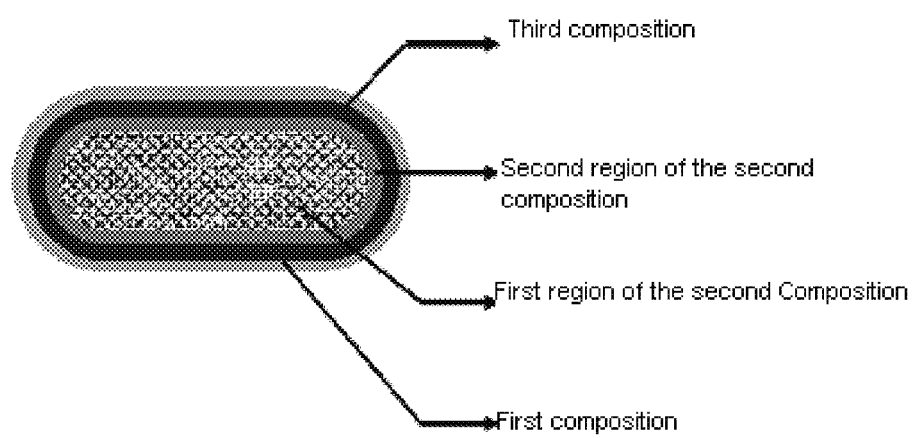

FIG. 4 depicts one of the embodiments of the controlled release drug delivery system used in the method of the present invention. The controlled release drug delivery system is in the form of a coated capsule. The first region of the second composition is in the form of a hard gelatin capsule filled with baclofen and other excipients. The second region of the second composition is a sub coating applied on the filled hard gelatin capsules. The sub-coated second composition is further coated with the third composition which contains expandable components and film former. The third composition is further coated with a first composition.

DETAILED DESCRIPTION OF THE INVENTION

The term "morning" as it is used herein with respect to the dosing of the controlled release drug delivery system of the invention means that the controlled release drug delivery system is orally administered early in the day after the patient has awakened from overnight sleep, generally between about 6:00 am and 11:00 am. In one preferred embodiment, the dosing was done at 8:30 am, post breakfast which was given at 8:00 am.

The term "evening" as it is used herein with respect to the dosing of the controlled release drug delivery system of the invention means that the controlled release drug delivery system is orally administered later in the day before the human subject goes to bed for the night sleep, generally between about 7:00 pm and 10:00 pm, after the human subject has taken dinner. In one preferred embodiment, the dosing was done at 7:00 pm, post dinner which was given at 6:30 pm.

The term "immediate release" refers to release obtained from conventional dosage form of baclofen that are given more than once-a-day for delivering baclofen to a human subject in need thereof.

The term "baclofen" as used herein refers to 4-amino-3-(p-cholorophenyl)-butyric acid or its pharmaceutically acceptable salt thereof or its derivatives. The term includes R-baclofen, S-Baclofen and their mixtures including the racemate. The racemate refers to a mixture of R and S-baclofen in equal proportions.

The term "$C_{max}$" is the highest plasma concentration of the drug attained within the dosing interval, i.e. about 24 hours. Thus, when a drug delivery system used in an embodiment of the method of the present invention provides a bi-modal plasma profiles with two peaks then $C_{max}$ represents the higher plasma concentration.

The term "$C_{min}$" is the minimum plasma concentration of the drug attained within the dosing interval, i.e. about 24 hours.

The term "$T_{max}$" is the time period which elapses after administration of the composition at which the plasma concentration of the drug attains the highest plasma concentration of drug attained within the dosing interval (i.e. about 24 hours). Thus, when a drug delivery system used in an embodiment of the method of the present invention provides a bi-modal plasma profiles with two peaks, the time at which the highest $C_{max}$ achieved is considered at as the $T_{max}$.

The term "AUC" as used herein, means area under the plasma concentration-time curve, as calculated by the trapezoidal rule over the complete 24-hour interval.

The fluctuation index is calculated as $(C_{max}-C_{min})/C_{avg} \times 100$ wherein $C_{avg}$ is calculated as ratio of $AUC_{(0-24)}$ to 24 hours.

The total daily dose of baclofen or its pharmaceutically acceptable salt or its derivatives present in the controlled release drug delivery system used in practicing the method of the present invention, ranges from 1 mg to about 150 mg, preferably about 5 mg to about 80 mgs. The amount of the total daily dose may be slightly different depending upon the disease condition for which the system of the present invention is used. Also the dose is dependent on the derivative or salt of baclofen that is employed. For instance, when the system of the present invention is used to treat gastroparesis with the use of an enriched form of enantiomer of baclofen such as R-baclofen, the amount of the daily dose of baclofen that may be used may range from about 5 mg to 10 mg. In another instance, when the system of the present invention is used to treat a disease condition related to alcohol related disorders, the amount of the total daily dose of baclofen may range from 10 mg to 120 mg. In certain cases, the dose of the baclofen may be titrated and increased from a lower range to a higher range, depending upon the need. For example, in an embodiment wherein the controlled release drug delivery system used in treating alcohol craving and intake, baclofen is given initially at a daily dose of 15 mg for initial few days and then the amount of total daily dose is increased to 30 mg to 40 mg for later period of treatment.

In one embodiment of the present invention, when the method uses controlled release drug delivery system, the system is administered in the fed condition. It is known that the pH of the gastric contents in the fed condition is about 4.3-5.4 whereas in the fasted state the pH of the gastric contents is about 1.4-2.1 (See T. T. Kararli, Biopharm. Drug. Disposition, 16, 351-380, 1995). Since the controlled release drug delivery system is, according to the invention, administered in the fed condition, in order to mimic the swelling characteristics and the retention in the stomach, the in vitro studies, such as measurement of the swelling index and/or the in vitro dissolution of baclofen or its pharmaceutically acceptable salt is determined at a pH of about 4.5, for example, in an aqueous medium of acetate buffer that provides a pH of 4.5.

Referring to FIG. 3, it is evident from the graph that the absorptive phase of baclofen lasts longer when the controlled release drug delivery system of baclofen is administered in the evening. Whereas absorption continues upto at least about 5 hrs in the case of morning dosing as reflected by the time of occurrence of a second peak in the plasma profile, absorption can be seen to be prolonged and continue at least upto about 12 hrs after evening dosing. This was an unpredicted and surprising finding. It was also evident and pleasantly surprising that after the occurrence of the second peak in the plasma level profile, the plasma concentration declined very rapidly in the case where the controlled drug delivery system was administered in the morning but declined comparatively slowly when the controlled drug delivery system was administered in the evening. Further it was observed as shown in Table 13 that the mean plasma concentration achieved during the later half of the dosing interval at steady state, were higher when the system was administered with meals in the evening according to the invention as compared to the mean plasma concentration achieved after administration in the morning. Thus, the method of the present invention provides an improved therapy during the later half of the dosing interval. Particularly, there is an improved therapy in controlling the early morning symptoms of the disease condition.

Figure 2:
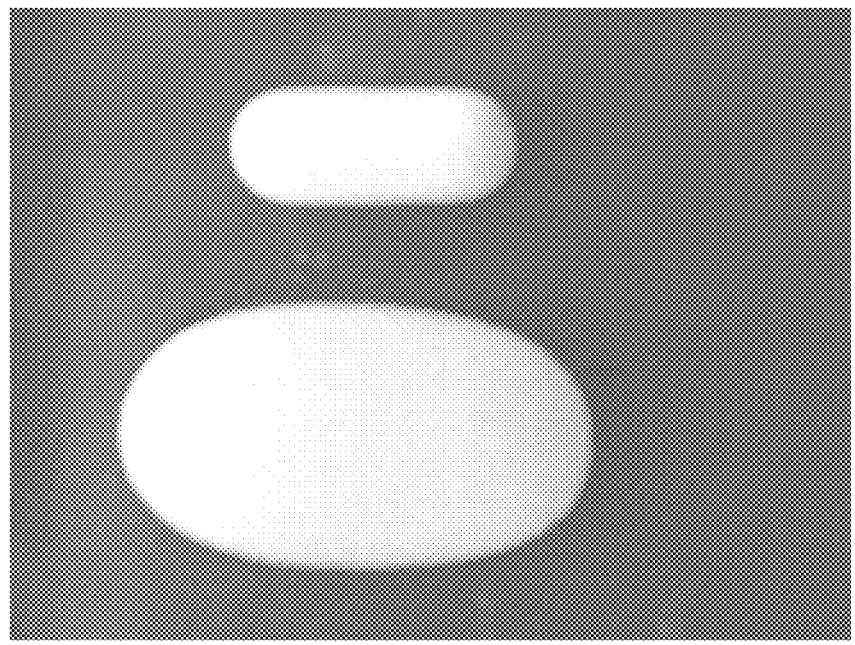
FIG. 2 illustrates a gastric retention controlled release drug delivery system in the form of capsules in the unswollen state and expanded due to swelling upon contact with aqueous medium for 6 hours.

FIG. 2 illustrates an embodiment of a gastric retention controlled release drug delivery system in the form of a swellable capsule useful in the method of the present invention. The swelling or expandable nature of the capsule is depicted by the photographic images of the coated capsule in 4.5 acetate buffer at the end of 6 hours. The initial dimensions were 22.65 mm in length and 8.92 mm in diameter. At the end of 6 hours the capsules were swollen and expanded to a length of 38.23 mm and 19.79 in diameter. It is known that the open pylorus has a diameter of ~15 mm in humans and objects greater than this size will have a difficulty in passing into the intestine (Stanley S. Davis in Drug Discovery Toady, Volume 10, No 4, February 2005, page 249-257).

Aspects of the present invention provide a method of treating a disease condition susceptible to baclofen therapy, said method comprising orally administering once-a-day in the evening a controlled release drug delivery system comprising baclofen or its pharmaceutically acceptable salt or its derivatives and pharmaceutically acceptable excipients.

A person skilled in the art will understand that an oral controlled release drug delivery system that does not itself possess the characteristics for gastric retention (as distinct from controlled release) can be retained in the stomach by extraneous means (that means not forming a part of, or not directly associated with, the, oral controlled release drug delivery system). Gastric retention may be achieved, for example, by co-administering agents that slow the gastric motility or utilizing any alternate means that reduces gastric motility. The present invention therefore encompasses not only the gastric retention controlled release drug delivery system (as a single dosage form) but also any other controlled release drug delivery system that gets retained in the stomach not because of it's own characteristics, but because of other factors extrinsic or external to the drug delivery system. Examples of agents that may be used to enhance the gastric retention of the controlled release drug delivery system by reducing gastric motility include, but are not limited to, amylin agonist like pramlintide, exendins and its analogs, exenatide and its derivatives, atropine and related compounds, antimuscarinic agents like propantheline, pirenzepine, hyoscine hydrobromide, antidiahhoeral compounds such as diphenoxylate, loperamide, octreotide, opium and any other active ingredient that causes reduction in the gastric motility or active ingredients that show reduction in gastric motility as one of the side effects.

In one embodiment, the controlled drug delivery systems useful in the practice of the present invention are typically characterized by release of about 30% to 40% of baclofen or its pharmaceutically acceptable salt in first hour in acidic media; about 50% in 4 hours; about 60% in 8 hours. The method of the present invention preferably provides a mean plasma concentration of baclofen at 16 hrs post administration in the range of about 40% to 90% of the mean peak plasma concentration, more preferably, about 55% to 80% of the mean peak plasma concentration. Further the method provides a fluctuation index of less than 200, preferably, less than 170 wherein fluctuation index is calculated as $(C_{max}-C_{min})/C_{avg} \times 100$ wherein $C_{avg}$ is calculated as AUC $_{(0-24)}/24$.

In one particular embodiment, the controlled drug delivery system of baclofen of the present invention produces a bi-modal plasma concentration-time profile (i.e., two distinct peaks) wherein a first peak in the plasma concentration is obtained at an earlier time between 2 hours to 8 hours, preferably 2 to 4 hours and the second peak is obtained at a later time point of time at about 8 hours to 18 hours, preferably 10 to 14 hours when orally administered to human subjects. Such a bi-modal plasma concentration-time profile may be advantageous in that it provides a second peak of baclofen at a time point of about 8 hours to 18 hours, preferably, about 12 hours. The profile is particularly useful in relief of early morning symptoms of the disease condition. The method of the present invention provides a therapeutic benefit which is assured at the time of awakening when the symptoms are generally more pronounced. It would be most beneficial to have highest peak plasma concentrations around the time of most frequent occurrence of symptoms. In one instance, the method of the present invention allows administration of the controlled release drug delivery at night time before sleep and provides a second plasma peak of baclofen at much later point of time which coincides with the wakening time where the system achieves therapeutic plasma levels at the more appropriate time. The appearance of the second peak is important for providing an optimum relief of early morning symptoms of the disease condition. For example, when the method of the present invention is practiced by administering a controlled release drug delivery system of baclofen or its pharmaceutically acceptable salt or its derivatives, to a patient in the evening, for example at about 6:00-about 8:00 pm, for relief of the symptoms over a duration of 24 hrs with high plasma levels of baclofen sustained in the next morning, for example, between about 7:00 am and about 11:00 am, particularly for optimum relief of early morning symptoms.

In certain embodiments, the controlled release drug delivery system is in the form of coated particles comprising baclofen or its pharmaceutically acceptable salt. The coated particles can be in the form of beads, granules, mini tablets. The drug may be present along with the excipients or may be loaded onto the particles. The particles can consist of the encapsulation of thousands of micro-particles, each measuring 200-500 micrometers in diameter. These microparticles can be delivered in caplets.

In another embodiment, the controlled release drug delivery system is in the form of matrix systems wherein the baclofen or its pharmaceutically acceptable salts are embedded in a matrix comprising polymers that retard the release of the drug. The polymer that may be used in the matrix of the controlled release drug delivery system may be selected from hydrophilic polymers, hydrophobic material like waxes and the like and mixtures thereof.

In certain embodiments, the controlled release drug delivery system used in the method of the present invention is designed such that it is retained in the stomach because of the characteristics of the formulation i.e. because of particular features of the system incorporated into the design of the system. The features by which the controlled release drug delivery system is retained in stomach for longer period of duration may be because of various mechanisms such as either the floating nature of the system or the swelling and expanding nature of system or bio-adhesive nature of systems or due to special shapes of the system, all leading to retention of the system in the gastric environment.

Following are the embodiments of the gastric retention controlled release drug delivery system that are used in practicing the method of the present invention.

In one embodiment, the system is expandable systems. This type of system is easily swallow able and reaches a significantly larger size in the stomach due to swelling or unfolding processes that prolong their gastric retention. After the complete release of the active ingredient, their dimensions are minimized with subsequent evacuation from the stomach. Gastroretentivity is enhanced by the combination of substantial dimensions with high rigidity of the dosage form to withstand the peristalsis and mechanical contractility of the stomach.

In alternate embodiment, the system can be a bio or muco-adhesive system. These types of systems are used as a delivery device within the lumen to enhance drug absorption in a site specific manner. This approach involves the use of bioadhesive polymers, which can adhere to the epithelial surface in the stomach. Gastric mucoadhesion does not tend to be strong enough to impart to dosage forms the ability to resist the strong propulsion forces of the stomach wall. The continuous production of mucous by the gastric mucosa to replace the mucous that is lost through peristaltic contractions and the dilution of the stomach content also seem to limit the potential of mucoadhesion as a gastroretentive force. Some of the most excipients that may be used in these systems to impart bioadhesion include, but are not limited to, polycarbophil, carbopol, lectins, chitosan and gliadin and the like and mixtures thereof.

In yet another embodiment of the present invention, the systems are based on floating mechanism. This type of drug delivery system has a bulk density less than gastric fluids and thus remains buoyant in the stomach without affecting gastric emptying rate for a prolonged period of time. While the system is floating on the gastric contents, the drug is released slowly at the desired rate from the system, after release of drug; the residual system is emptied from the stomach. This results in an increased gastric retention time and a better control of the fluctuations in plasma drug concentration. This particular type of system can be obtained by use of either non-effervescent materials or by use of gas-generating material. When such systems are based on non-effervescent materials, these types of systems, after swallowing, swells unrestrained via imbibitions of gastric fluid to an extent that it prevents their exit from the stomach. One of the formulation methods of such dosage forms involves the mixing of the drug with a gel, which swells in contact with gastric fluid after oral administration and maintains a relative integrity of shape and a bulk density of less than one within the outer gelatinous barrier. The air trapped by the swollen polymer confers buoyancy to these dosage forms. Excipients used most commonly in these systems include hydroxypropyl methyl cellulose (HPMC), polyacrylate polymers, polyvinyl acetate, Carbopol, agar, sodium alginate, calcium chloride, polyethylene oxide and polycarbonates.

When the systems are gas-generating or effervescent type, then these buoyant systems utilize matrices prepared with swellable polymers such as methocel, polysaccharides (e.g., chitosan), effervescent components (e.g., sodium bicarbonate, citric acid or tartaric acid). The system is so prepared that upon arrival in the stomach; carbon dioxide is released, causing the formulation to float in the stomach. Other materials that may be used include sodium alginate and sodium bicarbonate, multiple unit floating pills that generate carbon dioxide when ingested, floating mini capsules with a core of sodium bicarbonate, lactose and polyvinylpyrrolidone coated with hydroxypropyl methylcellulose (HPMC), and floating systems based on ion exchange resin technology.

In certain embodiments, when the controlled release drug delivery system is in the form of a gastric retention drug delivery system, the system may be superporous hydrogels or lipid carrier matrix or may be based on foam based technology. When the system is in the form of superporous hydrogels, the polymers that are used may be crosslinked polymers such as polyacrylic acid, polyacrylamide, poly(N-isoproyl-acrylamide), polyethylene oxide, poly(hydroxyethyl methacryalate), polyvinylpyrrolidone, poly(vinyl alcohol) and carboxymethylcellulose. These hydrogels have the ability to absorb water, and if the water content absorbed exceeds 95% of the total weight, it is called supersabsorbent hydrogel. The imbibition of water by the hydrogel creates a space in the structure which is known as effective pore size. The pore size of the hydrogel varies from 10 to 100 manometers for microporous and 100 nanometers to 10 micrometers for macroporous hydrogels. In one embodiment, the superporous hydrogels are prepared by addition of a monomer, initiator, and cross-linker. The monomer is polymerized to form superporous hydrogel having a large pore size. In preferred embodiment, superdisintegrants such as crosslinked Ac-Di-Sol, Prmojel and crospovidone are utilized as a composite material for the preparation of superporous hydrogel composite. The mechanical properties superporous hydrogel can be further improved by acidification of the ionizable groups of the polymer, which then enables the superporous hydrogel to withstand stresses of gastric contractions.

In yet another embodiment, the baclofen or its pharmaceutically acceptable salt are incorporated in a lipid carrier matrix. Such matrix systems have numerous advantages such as no additional solvent requirement for solubilization of drug, ease of availability, biocompatibility, biodegradability. The lipid matrix that may be excipients selected from a group consisting of glycerides and polyethylene glycol (PEG) esters. One excipient that is commercially available under the brand name of Gelucire is suitable according to the present invention. Various other lipid matrix systems may be employed to arrive at the bi-modal release pattern of baclofen when the patient administers the controlled release drug delivery system of the present invention.

In other embodiments of the present invention, a controlled release drug delivery system is in the form of matrix core that are dependent at least in part upon the diffusion and/or erosion properties of excipients within the composition. In this embodiment controlled release matrices contain an effective amount of a baclofen or its pharmaceutically acceptable salt. The amount of the baclofen present in the controlled release matrix can vary in an amount of from 40% to 90% by weight of the matrix tablet dry weight. For example, in certain embodiments baclofen or its pharmaceutically acceptable salts is present in an amount from 60% to 80%, and in other embodiment at 70% by weight of the matrix tablet dry weight. The controlled release matrix can be multiparticulate or uniparticulate, and can be coated with at least one functional or non-functional coating, or an immediate release coating containing a baclofen salt or other drug. Functional coatings include by way of example controlled release polymeric coatings, enteric polymeric coatings, and the like. Non-functional coatings are coatings that do not affect drug release but which affect other properties (e.g., they may enhance the chemical, biological, or the physical appearance of the controlled release formulation).

A preferred embodiment of such as controlled release drug delivery system useful in the practice of the present invention swells in a dimensionally unrestrained manner to increase its size to promote gastric retention of the system in the stomach. It may be noted that this is just one way of achieving the gastric retention of the controlled release drug delivery system and is provided as an illustration, by way of example only. Any other suitable means of gastric retention that leads to the desired plasma levels as described above are the may be applied in the practice of the present invention. The swelling and therefore, in turn the measurement of the gastric retention may be done by various ways, for example, in vivo by gastroscopy or radiology such as scintiographic studies or by in vitro methods such as for example, measurement of the swelling index of the controlled release drug delivery system.

Those embodiments where the gastric retention controlled drug delivery system is based on the expanding and swelling, a swelling capacity can be an indicator of gastric retention. According to one useful procedure, in order to estimate the swelling capacity, the dimensions such as diameter and height of the system were measured with the help of Vernier Calipers. The dosage form may be placed in a USP dissolution apparatus (Type II-Paddle type of apparatus) in pH 4.5 acetate buffer at 37±0.5° C. at 50 rpm. The dimensions of the dosage form are measured initially and then placed into the dissolution apparatus. At specified time intervals, the dissolution apparatus was stopped and the dosage form was removed with the help of spatula in a Petri-dish and the dimensions were recorded. The swelling index may be determined as a ratio of volume at particular time to initial volume. Volume may conveniently be calculated by applying formula for volume of cylinder, assuming capsules are of at least approximately cylindrical shape. Volume of Cylinder–$\pi r^2 h$, where r=diameter/2, h=length of capsule. Swelling Index is calculated as the ratio of the final volume and the initial volume. Generally, the swelling index of the gastric retention controlled drug delivery system used in the method of the present invention ranges from 2 to 20, preferably 5 to 15. One embodiment of the present invention, in which the gastric retention controlled release drug delivery system is a coated capsule the swelling index at 1 hour to 8 hours in acetate buffer is recorded in Table 7.

FIG. 2 illustrates an embodiment of the controlled release drug delivery system in the form of capsules useful in the practice of the method of the present invention. The swelling or expandable nature of the capsule is depicted by the photographic images of the coated capsule in pH 4.5 acetate buffer at the end of 6 hours. The initial dimensions were 22.65 mm in length and 8.92 mm in diameter. At the end of 6 hours the capsules were swollen and expanded to a length of 38.23 mm and 19.79 in diameter. It is known that the open pylorus has diameter of 12 mm-18 mm in humans and objects greater than this size will have a difficulty in passing into the intestine (See Research J. Pharm. and Tech.; October-December 2008 pp. 345-348). The gastric emptying time and thereby, the retention of the dosage form of any discrete dosage form is delayed in the presence of food. At the end of the fed mode, a change in the motility pattern of the stomach occurs towards the fasting mode, and it is believed that a discrete dosage form is swept away by the housekeeper wave. However, size achieved after expansion does remain an important factor in the present system and preferably the volume is more than 9000 $mm^3$ at the end of 4 hours.

Embodiments of controlled release drug delivery system useful in the method of the present invention are described in our previous United States patent publications US 20040180088 A1 and United States patent publication US20080107732A1, which are incorporated herein by reference.

According to one embodiment of the present invention, the method comprises orally administering once-a-day in the evening a gastric retention controlled release drug delivery system comprising baclofen or its pharmaceutically acceptable salt and pharmaceutically acceptable excipients wherein the gastric retention controlled release drug delivery system comprises a first composition having an immediately releasing fraction of the baclofen dose which is released within about 1 hour when tested in one liter of 4.5 pH acetate buffer in USP type II dissolution apparatus with sinkers rotating at a 50 rpm and at a temperature of 37±0.5° C. and a second composition having a slow release fraction of the baclofen dose wherein the first composition and the second composition occupy separate regions in the system, and at least one of the excipients in the controlled drug delivery system is selected from the group consisting of swellable polymer, gas generating agent, superdisintegrant and mixtures thereof, which excipient causes the system to swell in a dimensionally unrestrained manner to increase its size to promote gastric retention of the system in the stomach.

In another embodiment, the gastric retention controlled release drug delivery system is in the form of a coated capsule. In this particular embodiment, the second composition includes at least two separate regions, first region comprising baclofen or its pharmaceutically acceptable salt and a second region comprising an excipient selected from the group consisting of swellable polymers, gas generating agents, super-disintegrants and mixtures thereof.

The second composition includes at least two separate regions, first region comprising baclofen or its pharmaceutically acceptable salt. The first region of the second composition comprises a slow release fraction of the total dose of baclofen that is present in the gastric retention controlled drug delivery system used in the method of the present invention. The amount of baclofen present in second composition is designed to release in a controlled or slow manner. Generally the ratio of the immediately releasing fraction and the slow release fraction ranges from about 1:1 to 1:3, preferably 1:1 to 1:1.5. For example, in one embodiment when the gastric retention controlled release drug delivery system comprises a total dose of 60 mg of the dose, 35 mg of baclofen is present in the second composition and 25 mg of baclofen is present in first composition.

In this particular construction, the first region of the second composition comprises along with baclofen or its pharmaceutically acceptable salts, excipients selected from the group consisting of swellable polymers, gas generating agents and superdisintegrants or mixture thereof. In particularly embodiment, the first region of the second composition is in the form of a core of hard gelatin capsule filled with a mixture comprising a fraction of the baclofen, one or more excipients selected from the group consisting of swellable polymers, gas generating agents and superdisintegrants. The second region of the second composition comprises one or more excipients selected from the group consisting of swellable polymers, gas generating agents and superdisintegrants. The difference between the first region and the second region is that the first region contains baclofen and the second region does not contain baclofen.

Categories of the swellable polymers that may be used in the gastric retention controlled release drug delivery system used in the method of the present invention include, but are not limited to, cellulose derivatives, alginic acid and its derivatives, starch and its derivatives, gums, polyacrylic acid and the like and mixtures thereof. Cellulose ethers and esters are available in different viscosity grades. The grades may be expressed in terms of viscosity and/or in terms of number average molecular weight. The viscosity and number average molecular weight are related to each other. Such grades of the cellulose ethers are described in terms of number average molecular weight and degree of polymerization. The cellulose derivatives that may be used include, but are not limited to, cellulose ethers, cellulose esters and the like. Examples of suitable cellulose ethers include hydroxypropyl methyl cellulose, available from Dow Chemicals under the trade name Methocel, hydroxypropyl cellulose low substituted, hydroxypropyl cellulose, available from Aqualon under the trade name Klucel, hydroxyethyl cellulose, available from Aqualon under the trade name Natrosol and Cellosize available from Amerchol Corporation, carboxymethylcellulose sodium, available under the trade name Akucell. Methocel is available in various viscosity grades. The typical viscosities, unless specified, are expressed for a 2% w/v aqueous solution measured at 20° c. For example, K100 LVP having viscosity ranging from about 80 to about 120, K4MP having medium viscosity ranging from about 3000 to about 5600, K15 M having high viscosity ranging from about 12,000 to about 21,000; K100 MP having high viscosity ranging from about 80,000 to about 120,000; Klucel is available in different viscosity grades. For example, Klucel HF (1% w/v) solution shows a viscosity ranging from about 1500 to about 3000. Klucel MF (2% w/v) solution shows a viscosity ranging from about 4000 to about 6500. Klucel GF (2% w/v) solution shows a viscosity ranging from about 150 to about 400. Klucel JF (5% w/v) solution shows a viscosity ranging from about 150 to about 400. Klucel LF (5% w/v) solution shows a viscosity ranging from about 75 to about 150 and Klucel EF (10% w/v) solution shows a viscosity ranging from about 200 to about 600. Different types of viscosity grades of Natrosol 250 are available such as HHR having viscosity 1% w/v solution 3400 to about 5000, H4R having viscosity ranging from about 2600 to about 3300, HR having viscosity ranging from about 1500 to about 2500 and MHR having viscosity ranging from about 800 to about 1500. Low viscosity grades of Natrosol include, but are not limited to, MR, KR, GR, ER, JR and LR. Carboxymethyl cellulose is available as low viscosity Akucell AF 0303 (1% w/v) showing a viscosity ranging from about 10 to about 15 mPas. The medium viscosity grade of Akucell AF2785 shows a viscosity ranging from about 1500 to about 2500. The 1% w/v solution of high viscosity grade of Akucell AF3085 shows a viscosity ranging from about 8000 to about 1200. Some preferred dosage forms for use in the practice of the present invention use hydroxypropyl cellulose (HPC) having viscosity of about 100,000 cps. It is also possible to use Alginic acid which is available in different viscosity grades. The viscosities depend on the molecular weight. Typically, a 0.5% w/w aqueous dispersion shows a viscosity of approximately 10 mPas while a 2% w/w aqueous dispersion shows a viscosity of approximately 2000 mPas. Sodium alginate is also available in different viscosity grades. Typically, a 1% w/v aqueous solution shows a viscosity of 20 to about 400 mPas. Polyvinyl pyrrolidone of high viscosity may be employed. Another example of a swellable polymer that may be used in a drug delivery system suitable for use in the method of the present invention is a pH dependent polymer that is soluble below about pH 5 and is swellable and permeable above pH 5. Preferably the pH dependent polymer is an acrylate polymer obtained by polymerizing dimethylamino ethyl methacrylate with neutral methacrylate esters. In a more preferred embodiment of the present invention the pH dependent polymer is a polymer obtained by polymerization of the monomers namely, butyl methacrylate, 2-dimethyl aminoethyl methacrylate and methyl methacrylate. This polymer, poly(butyl methacrylate, (2-dimethyl aminoethyl) methacrylate, methyl methacrylate) may be prepared from different molar ratios of the monomers. However, preferably, the butyl methacrylate, 2-dimethyl aminoethyl methacrylate and methyl methacrylate molar ratio is about 1:2:1. This preferred polymer butyl methacrylate, 2-dimethyl amionethyl methacrylate and methyl methacrylate with a molar ratio of about 1:2:1 is available in different physical forms under the trade names Eudragit E 100, Eudragit E 12.5 and Eudragit EPO. Eudragit E 100 is in the form of granules, Eudragit E 12.5 is available in the form of 12.5% w/v solution in an organic solvent and Eudragit E PO is available in powder form.

The swellable polymer may be present in an amount ranging from about 1% to about 40%, preferably about 5% to about 30% and most preferably about 10% by weight of the gastric retention controlled release drug delivery system used in the method of the present invention.

The gas generating agent used in the gastric retention controlled release drug delivery system of the present invention may include a single component that generates gas upon contact with the gastric fluid, or may include a gas generating couple. Gas generating components that may be used in the present invention include solids that liberate gas, especially carbon dioxide or nitrogen, for example under the action of body fluid or the hydrogen ions present therein. Examples include carbonates such as calcium carbonate, bicarbonates such as sodium or potassium bicarbonate, sulfites such as sodium sulfite, sodium bisulfite, or sodium metabisulfite, and the like, ammonium cations or sodium azide or mixtures thereof. These salts may be used alone or in combination with an acid source as a gas generating couple. The acid source may be an edible organic acid, a salt of an edible organic acid, or mixtures thereof. Examples of organic acids that may be used include citric acid, malic acid, succinic acid, tartaric acid, fumaric acid, maleic acid, ascorbic acid, glutamic acid, alginic acid, acrylic acid and their salts, and mixtures thereof. Sodium bicarbonate is used as the preferred gas generating agent. The organic acid may also be a polymer, for example acrylic acid polymers and copolymers such as acrylate polymers available under the tradenames Carbopol®, Eudragit® L-100-55, Eudragit® S-100, Noveon® AA1, which react with carbonates or bicarbonates of alkali or alkali earth metal compounds to generate gas. These are generally used as auxiliary acid sources and may also have properties of themselves generating internal pressure by swelling when in contact with an aqueous medium. The gas-generating agent is used in an amount ranging from about 0.5% to about 50%, preferably in the range of 5% to about 10% by weight of the gastric retention controlled release drug delivery system used in the method of the present invention.

Examples of superdisintegrants that can be used in gastric retention drug delivery systems useful in the practice of the present invention include, but are not limited to, crosslinked sodium carboxymethyl cellulose, crosslinked polyvinylpyrrolidone, sodium starch glycolate, ion exchange resins and mixtures thereof. The superdisintegrants may be used in an amount ranging from about 0.5% to about 30%, preferably about 3% to about 10% by weight of the gastric retention controlled release drug delivery system used in the method of the present invention.

In another embodiment, the first region of the second composition may further include one or more rate controlling excipients. Examples of release rate controlling excipients include, but are not limited to, water insoluble polymers and hydrophobic materials such as waxes. Hydrophobic materials apart from acting as release rate controlling excipients, because of their low density, can also enhance the gastric retention of the coated capsule of the present invention. Examples of the hydrophobic materials that may be used include, but are not limited to, waxes, carnauba wax, vegetable wax, fruit wax, microcrystalline wax, bees wax, hydrocarbon wax, paraffin wax, cetyl esters wax, nonionic emulsifying wax, anionic emulsifying wax, candelilla wax, stearyl alcohol, cetyl alcohol, cetostearyl alcohol, lauryl alcohol, myristyl alcohol, hydrogenated vegetable oil, hydrogenated castor oil, a fatty acids, a fatty acid esters, or mixtures thereof. Generally, the amount of the hydrophobic material present in second region of the second composition of the gastric retention drug delivery system used in the method of the present invention ranges from about 0.1% to about 10% by weight of the gastric retention controlled release drug delivery system used in the method of the present invention.

Apart from the above mentioned excipients, water soluble materials such as mannitol, lactose, lactitol, xylitol, sucrose or mixtures thereof or any other sugar alcohol may also be present in the third second composition of the gastric retention controlled release drug delivery system. When present, the amount of such material may be from about 0% to about 60%, preferably about 15% to about 50% by weight of the second composition of the gastric retention controlled release drug delivery system used in the method of the present invention.

In one particular embodiment, the weight ratio of second region of the second composition to the first region of the second composition is about 25:1. The weight ratio of third composition to the second composition is about 25:1.

In another embodiment, the gastric retention controlled release drug delivery system comprises a third composition. The third composition is present in between the first composition and the second composition. In certain embodiment, when the second composition is in the form of a coated capsule, the third composition is in the form of a coating that is applied to the second composition. The third composition is applied to the second composition in the form of coating surrounding the second composition. The third composition comprises a water insoluble polymer and one or more excipients selected from the group consisting of swellable polymers, gas generating agents and superdisintegrants. The water insoluble polymer present in the third composition are insoluble in gastric milieu and is selected from the group consisting of ethyl cellulose, methacrylic acid-ethyl acrylate copolymers, polyacrylic acid and mixtures thereof. In preferred embodiments, the third composition forms a film capable of expanding and maintaining its physical integrity in the gastric milieu.

In certain embodiments, in addition to the water insoluble polymers that are insoluble in gastric milieu, the third composition may further comprise one or more swellable polymers such as Carbopol® polymers, Pemulen™ polymeric emulsifiers and Noveon® polycarbophils. In one particular embodiment, a high molecular weight acrylic acid polymer crosslinked with divinyl glycol is employed. This may be used in amount ranging from about 0.1% by weight to about 10% by weight, preferably about 1% to about 2% by weight of the gastric retention controlled release drug delivery system. In preferred embodiments, the third composition is in the form of a membrane or a film that surrounds the second composition which is either in the form of a compressed core or a capsule filled with excipients. The presence of the excipients of third composition, cause the film to stretch and expand in size to form a balloon like system. The membrane or the film made up of the third composition provides strength and elasticity to the system in the gastric milieu. Because of the elastic and stretchable nature of the membrane, the system can withstand the contractions of the stomach and not break open and continues to release baclofen over a desirable period of time. In another preferred embodiment, where a bioadhesive polymer such as polycarbophil is incorporated, the system in addition to swelling also achieves bioadhesive effect causing gastric retention. The membrane of the third composition may comprise of additional plasticizers which adds to the stretchable elastic nature of the polymer, causing better expansion and stretching of the system leading to increase in size sufficient enough to cause gastric retention.

The first composition present in gastric retention controlled release drug delivery system used in the method of the present invention, comprises an immediately releasing fraction of the baclofen dose which is released within about 1 hour when tested in one liter of 4.5 pH acetate buffer in USP Type II dissolution apparatus with sinkers rotating at a 50 rpm and at a temperature of 37±0.5° C. This first composition occupies a region separate within gastric retention controlled drug delivery system which is physically distinct from the region occupied by the second composition. In one embodiment, the first composition is present in the form of a coating wherein the composition comprises an excipient that does not hinder in the immediate release of the fraction of the baclofen dose. Preferably, when the first composition is in the form of a coating, the first composition comprises water soluble polymers such as low viscosity water soluble polymers used in the top coating for example, hydroxypropyl methyl cellulose or methyl cellulose or any other cellulose derivative of very low viscosity which does not hinder the immediate release of fraction of the total dose baclofen present in the gastric retention controlled release drug delivery system.

According to another aspect of the invention, a method of the present invention useful for optimum relief of early morning symptoms of the disease condition is provided, said method comprising administration of a controlled release drug delivery system of baclofen or its pharmaceutically acceptable salt, to the patient in the evening example at about 6:00-about 8:00 pm, for relief of the symptoms over a duration of 24 hrs with high plasma levels of baclofen sustained in the next morning, for example between about 7:00 am and about 11:00 am, particularly for optimum relief of early morning symptoms.

In one embodiment, a randomized, open-label, two-treatment, two-period, two-sequence, multiple dose, crossover study was conducted to assess bioavailability and steady state pharmacokinetics of baclofen 30 mg capsules prepared as per Example 1 was given once daily, under fed (normal meal) conditions, for 8 consecutive days in patients suffering from spasticity. Baclofen 10 mg immediate release tablets were given three times a day at 8 hour interval, with the initial dose administered under fasting condition, for 8 consecutive days, in 24 spastic subjects receiving stable daily doses of baclofen. In one study, the dosing of the baclofen 30 mg capsules (Test=t) was done in morning time and in another study, the dosing of the baclofen 30 mg capsules was done in evening time, both on fed condition.

The pharmacokinetic results in terms of bioavailability, i.e $C_{max}$, $T_{max}$, AUC were recorded and compared with the bioavailability parameters achieved by equivalent dose of immediate release baclofen that was administered three times a day (Reference=R). In one embodiment of the present invention, the method of treating spasticity was practiced. In this particular embodiment it was surprisingly found that the spastic patients showed better pharmacokinetic profile when the controlled drug delivery system of the present invention was administered by spastic patients on fed state in the evening in comparison to the pharmacokinetic profile achieved when the controlled drug delivery system of the present invention was administered on fed state in the morning wherein the study was a two way crossover, wherein one arm administered the controlled drug delivery system of the present invention and the other arm administered equivalent dose of baclofen in the form of immediate release tablets administered three times a day.

While the present invention is disclosed generally above, additional aspects are further discussed and illustrated with reference to the examples below. However, the examples are presented merely to illustrate the invention and should not be considered as limitations thereto.

EXAMPLE 1

This example represents an embodiment of the controlled release drug delivery system which is gastric retention drug delivery system comprising baclofen. It is prepared according to formulae given Table 1 below.

TABLE 1 first region of second composition

| S. No. | Ingredients | Qty in mg | % by weight of the drug delivery system |
|---|---|---|---|
| 1 | Baclofen | 35 | 3.25 |
| 2 | Mannitol | 324 | 30.12 |
| 3 | Hydroxypropyl Cellulose -mw 1150; apparent viscosity 1500-3000 at 1% w/v | 80 | 7.43 |

TABLE 1-continued first region of second composition

| S. No. | Ingredients | Qty in mg | % by weight of the drug delivery system |
|---|---|---|---|
| 4 | Colloidal silicon dioxide | 5 | 0.46 |
| 5 | Talc | 12.5 | 1.66 |
| 6 | Magnesium stearate | 12.5 | 1.16 |
| 7 | Hydrogenated Vegetable oil | 20.0 | 1.86 |
| 8 | Mannitol | 46.0 | 4.27 |
| 9 | Water soluble protective film coating based on low viscosity hydroxypropylmethyl cellulose | 20.0 | 1.85 |

First Region of Second Composition

Table 1 gives the formula for the preparation of the first region of the second composition. The first region is the formulation that is filled into gelatin capsules. The polymer hydroxypropylmethyl cellulose, low viscosity that does not function as a rate controlling polymer but only serve as a aid in binding on slugging to process the slug. This formulation does not contain any excipient that is characterized as a rate controlling excipient.

Baclofen, Hydroxypropyl cellulose (HPC-HXF), Colloidal silicon dioxide and Mannitol (intra-granular) were sifted and collected together. The material was resifted through ASTM #40 sieved and collected. The sifted material was loaded into a suitable blender and mixed for a period of 10 minutes. Magnesium stearate and Talc were added as lubricants and further mixed for 5 minutes. The blend was slugged using 20 mm flat-faced round punches using a single rotary compression machine. The slugs were milled to achieve a particle size suitable for capsule filing. Opadry II Clear and mannitol were sifted. The hard gelatin capsules of size '0' capsules were filled with the milled material and added extragranularly to the milled blend.

TABLE 2 second region of second composition comprising a mixture of disintegrants, gas generating agent and water soluble polymer

| S. No. | Ingredients | qty in mg | % by weight of the drug delivery system |
|---|---|---|---|
| 10 | Alginic acid | 60.06 | 5.60 |
| 11 | Sodium bicarbonate | 15.58 | 1.45 |
| 12 | Sodium starch glycolate | 30.03 | 2.79 |
| 13 | Mannitol | 15.00 | 1.40 |
| 14 | Povidone | 18.36 | 1.70 |
| 15 | Basic butylated methacrylate Copolymer | 18.38 | 1.70 |
| 16 | Talc | 3.89 | 0.36 |
| 17 | Polysorbate | 1.22 | 0.11 |
| 18 | Isopropyl alcohol (IPA) | q.s | q.s |

Second Region of Second Composition

Table 2 gives the formula for the preparation of the second region of the second composition which is also referred to as subcoat composition. The filled capsules were coated with a sub coat composition prepared by dispersing Eudragit, polyvinyl pyrrolidone, alginic acid, Sodium bicarbonate, Sodium starch glycolate, Mannitol 25 and Talc in isopropyl alcohol containing polysorbate 20. The dispersion was passed through a coarse screen to ensure homogenous dispersion. The filled capsules were loaded into a suitable perforated coating pan (36") and the capsules were coated with a second subcoat composition to a weight gain of about 25%.

TABLE 3

Third composition of film forming polymer insoluble in gastric milieu and one or more disintegrants and/or gas generating agents

| S. No. | Ingredients | Qty in mg | % by weight of the drug delivery system |
|---|---|---|---|
| 19 | Polycarbophil | 8.95 | 0.83 |
| 20 | Methacrylic acid Copolymer, Type C | 66.15 | 6.14 |
| 21 | Sodium bicarbonate | 17.88 | 1.66 |
| 22 | Sodium starch glycolate | 21.50 | 1.99 |
| 23 | Mannitol | 71.52 | 6.64 |
| 24 | Polyethylene glycol | 2.69 | 0.25 |
| 25 | Diethyl Phthalate | 8.95 | 0.83 |
| 26 | Polysorbate | 1.07 | 0.09 |
| 27 | Talc | 4.46 | 0.41 |
| 28 | Isopropyl alcohol (IPA) | q.s | q.s |

Table 3 provides the details of the third composition of film forming polymer insoluble in gastric milieu and one or more disintegrants and/or gas generating agents The sub coated filled capsules were further coated with a coating dispersion for Film-coating comprising a water insoluble polymer. The coating suspension was prepared by dispersing ingredients of table 3 in isopropyl alcohol. Sequentially the dispersion was screened to ensure uniform homogeneous dispersion and absence of lumps. The sub-coated capsules were loaded into a suitable perforated coating pan (48") and were coated to a weight gain of about 25% using the coating solution.

TABLE 4 first composition of gastric retention controlled drug delivery system

| S. No. | Ingredients | Amount in mg | % by weight of the drug delivery system |
|---|---|---|---|
| 29. | Baclofen | 25.00 | 2.3 |
| 30. | HPMC low viscosity | 35.00 | 3.25 |
| 31. | Purified water | q.s | |

Table 4 above provides a first composition comprising fraction of the baclofen in a protective thin film coating composition. The double layer coated capsules were further coated with a coating dispersion using commonly available Opadry ready to use composition in which baclofen was dispersed using an overhead stirrer.

The controlled release drug delivery system of example 1 were tested for in vitro dissolution in pH 4.5 buffer in USP Type II with sinkers, RPM 50, Temperature—37.5° C. as well as in pH 6.8 buffer. The results of the in vitro dissolution are given below:

TABLE 5

In vitro Dissolution results in 4.5 acetate buffer

| Time (hrs) | % Drug Release in pH 4.5 Buffer |
|---|---|
| 1 | 41 |
| 2 | 44 |
| 4 | 46 |
| 6 | 49 |
| 8 | 54 |
| 12 | 67 |
| 16 | 79 |
| 20 | 88 |
| 24 | 95 |

TABLE 6

In vitro dissolution results

| Time (hrs) | % Drug Release in pH 6.8 Buffer |
|---|---|
| 0.5 | 39 |
| 1.0 | 43 |
| 1.5 | 46 |
| 2.0 | 53 |
| 2.5 | 65 |
| 3.0 | 77 |
| 3.5 | 88 |
| 4.0 | 97 |
| 5.0 | 101 |
| 6.0 | 102 |

The gastric retention controlled drug delivery based on swelling and expanding mechanism, useful in the method of the present invention were checked for swelling index at various time points in pH 4.5 buffer. The capsules were allowed to swell under stirring using a USP Type assembly rotating at 75 rpm speed. Swelling Index was calculated as a ratio of volume at particular time to initial volume. Volume was calculated by applying formula for volume of cylinder, assuming capsules are of cylindrical shape. Volume of Cylinder=$\Pi r^2 h$, where r=diameter/2, h=Length of capsule. Swelling Index is calculated as the ratio of the final volume and the initial volume.

TABLE 7

Swelling index of the coated capsules of example 1

| Time (in hours) | Swelling Index Drug delivery system of example 1 | | | | | |
|---|---|---|---|---|---|---|
| | 1 | 2 | 3 | 4 | 5 | 6 |
| 1 | 3.15 | 3.78 | 3.96 | 3.40 | 4.14 | 3.20 |
| 2 | 4.12 | 4.09 | 5.44 | 4.20 | 5.46 | 4.83 |
| 3 | 5.38 | 5.97 | 6.38 | 5.76 | 6.67 | 6.15 |
| 4 | 6.77 | 7.33 | 7.00 | 6.90 | 7.92 | 7.48 |
| 5 | 8.13 | 9.02 | 8.79 | 8.96 | 10.05 | 9.68 |
| 6 | 10.31 | 10.61 | 9.97 | 10.08 | 11.37 | 10.91 |
| 7 | 12.46 | 12.29 | 11.24 | 12.63 | 11.94 | 13.39 |
| 8 | 12.87 | 12.94 | 12.11 | 14.18 | 13.54 | 13.69 |

The swelling nature of the coated capsule of the present invention is also depicted by the photographic images of the coated capsule in 4.5 Acetate buffer in the FIG. 2.

EXAMPLE 2

A gastric retention drug delivery system comprising baclofen was prepared as mentioned in Table 8 below.

TABLE 8

Composition details

| Ingredients | mg per weight of drug delivery system | % by weight of the drug delivery system |
|---|---|---|
| First region of the second composition | | |
| Baclofen | 22.5 | 5.49 |
| Fumaric acid | 10.0 | 2.44 |
| Mannitol | 264.5 | 64.5 |
| Hydroxypropyl cellulose | 68.0 | 16.59 |
| Sodium bicarbonate | 30.0 | 7.32 |
| Colloidal silicon dioxide | 5.0 | 1.22 |
| Talc | 5.0 | 1.22 |
| Magnesium stearate | 5.0 | 1.22 |

TABLE 8-continued

Composition details

| Ingredients | mg per weight of drug delivery system | % by weight of the drug delivery system |
|---|---|---|
| Second region of the second composition | | |
| Alginic acid | 54.35 | Coated to a weight gain of about 25% by weight of the core |
| Sodium bicarbonate | 10.87 | |
| Sodium starch glycolate | 27.17 | |
| Mannitol | 13.59 | |
| Polyvinylpyrrolidone | 16.30 | |
| Talc | 3.26 | |
| Polysorbate | 1.09 | |
| Third composition | | |
| Polycarbophil | 4.41 | Coated to a weight gain of about 18% by weight |
| Sodium bicarbonate | 8.82 | |
| Methacrylic acid copolymer | 35.29 | |
| Eudragit S-100 | 8.82 | |
| Mannitol | 35.29 | |
| Sodium starch glycolate | 10.29 | |
| Polysorbate | 0.59 | |
| Polyethylene glycol | 1.47 | |
| Talc | 2.35 | |
| Diethyl phthalate | 6.62 | |
| First composition | | |
| Baclofen | 7.5 | Coated to a weight gain of about 1.2% by weight of the coated core |
| Polyvinylpyrrolidone | 1.50 | |
| Talc | 2.25 | |
| Tween | 0.40 | |

Baclofen, fumaric acid, mannitol, hydroxypropyl cellulose, sodium bicarbonate, colloidal silicon dioxide, talc and magnesium stearate were mixed to obtain a blend and this was filled in size 0 hard gelatin capsules. The filled capsules were coated with a coating suspension containing alginic acid, sodium bicarbonate, sodium starch glycolate, mannitol, povidone, talc, polysorbate in isopropyl alcohol to a weight gain of about 25% by weight of the core capsules. This was followed by introduction of the outer coat using a coating solution comprising polycarbophil, sodium bicarbonate, methacrylic acid copolymer, Eudragit S-100, mannitol, sodium starch glycolate, polysorbate, PEG, talc and diethyl phthalate in isopropyl alcohol, the solution being coated to about 18% by weight. Finally, a top coat comprising baclofen, povidone, talc and Tween was introduced on the capsules to a weight gain of about 1.5%, using a coating solution in purified water.

EXAMPLE 3

A gastric retention drug delivery system comprising baclofen was prepared as mentioned in Table 9 below.

TABLE 9

| Ingredients | Quantity (mg/capsule) | (% w/w of the drug delivery system) |
|---|---|---|
| First region of the second composition | | |
| Baclofen | 22.5 | 5.49 |
| Fumaric acid | 10.0 | 2.44 |
| Mannitol | 200.5 | 48.90 |
| Polycarbophil | 108.0 | 26.34 |
| Sodium bicarbonate | 54.0 | 13.17 |
| Colloidal silicon dioxide | 5.0 | 1.22 |
| Talc | 5.0 | 1.22 |
| Magnesium stearate | 5.0 | 1.22 |

The first region of the second composition was obtained by blending the excipients listed in Table 10 with baclofen and filling it in a hard gelatin capsule. The capsule was then coated with a second region of the second composition and third composition similar to example 2 described above.

EXAMPLE 4

A gastric retention drug delivery system comprising baclofen was obtained as mentioned in Table 10 below.

TABLE 10

| Ingredients | mg per weight of drug delivery system | % w/w of the drug delivery system |
|---|---|---|
| First Region of the second composition | | |
| Baclofen | 22.5 | 3.38 |
| Fumaric acid | 10.0 | 1.50 |
| Mannitol | 264.50 | 39.77 |
| Crospovidone | 55.0 | 8.27 |
| Sodium bicarbonate | 30.0 | 4.51 |
| Silicified microcrystalline cellulose | 253.0 | 38.05 |
| Polyvinylpyrrolidone | 15.0 | 2.26 |
| Colloidal silicon dioxide | 5.0 | 0.75 |
| Talc | 5.0 | 0.75 |
| Magnesium stearate | 5.0 | 0.75 |
| Hydroxypropyl methylcellulose | 20.49 | |
| Second Region of the second composition | | |
| Alginic acid | 60.39 | Coated to a weight gain of about 20% by weight of the seal coated core |
| Sodium bicarbonate | 12.08 | |
| Sodium starch glycolate | 30.20 | |
| Mannitol | 15.10 | |
| Polyvinylpyrrolidone | 18.12 | |
| Talc | 3.62 | |
| polysorbate | 1.21 | |
| Third composition | | |
| Polycarbophil | 4.00 | Coated to a weight gain of about 12% by weight of the core with the seal coat and the subcoat |
| Sodium bicarbonate | 8.00 | |
| Methacryalic acid copolymer | 31.99 | |
| Eudragit S-100 | 8.00 | |
| Mannitol | 31.99 | |
| Sodium starch glycolate | 9.33 | |
| Polysorbate | 0.53 | |
| Polyethylene glycol | 1.33 | |
| Talc | 2.13 | |
| Diethyl phthalate | 4.00 | |
| First Composition | | |
| Baclofen | 7.5 | Coated to a weight gain of about 1.2% by weight of the coated core |
| Polyvinylpyrrolidone | 1.50 | |
| Talc | 2.25 | |
| Polysorbate | 0.40 | |

The coated tablets were obtained as mentioned in examples above. The core coated with the subcoat was placed in 100 ml of 0.01N HCl and pH 4.5 buffers. It was found that the sub-coated tablets remained at the base of the vessel and began to disintegrate after about 3 minutes, and fully disintegrated in about 6 minutes.

EXAMPLE 5

The controlled release drug delivery system was obtained as per Table 11 below.

TABLE 11

| Ingredients | Amount in mg per tablet | % by weight of the tablet |
|---|---|---|
| Baclofen | 20 | 2 |
| Lactose | 30 | 3 |
| Hydroxyethyl cellulose (HEC 250 H) | 400 | 4 |

TABLE 11-continued

| Ingredients | Amount in mg per tablet | % by weight of the tablet |
|---|---|---|
| Sodium starch glycolate | 150 | 15 |
| Sodium bicarbonate | 40 | 4 |
| Hydroxypropyl methylcellulose (3000-5600 mPaa) | 136 | 13.6 |
| Silicified microcrystalline cellulose | 90 | 9.0 |
| Talc | 24 | 2.4 |
| Polyethylene glycol (PEG 8000) | 10 | 1.0 |
| Hydroxypropyl methylcellulose (3000-5600 mPaa) | 100 | 10 |
| Coat | | |
| Baclofen | 10.0 | 1 |
| Low viscosity Hydroxypropyl methylcellulose aqueous coating | 45.0 | 4.5 |

The core of the controlled release drug delivery system was obtained by passing baclofen, lactose, hydroxyethyl cellulose, sodium starch glycolate, sodium bicarbonate and a part of HPMC K4M through ASTM (American Society for Testing and Materials) sieve #40 and mixing the ingredients to obtain a dry powder blend. An aqueous solution of HPMC K4M was then used to granulate the dry powder blend. The granules thus obtained were passed through a suitable sieve and dried. The dry granules were lubricated with a mixture of Prosolv SMCC 90, talc, PEG 8000 and HPMC K4M, and compressed to obtain the cores. The cores were then coated with an aqueous solution containing baclofen and Opadry II to obtain the gastric retention controlled drug delivery system of the present invention.

The tablets thus obtained were subjected to dissolution testing at 37° C. using United States Pharmacopoeia Type II (paddle) dissolution apparatus at 50 rpm. The dissolution medium used was 1000 ml of 0.1N HCl. The tablets achieved floatation in about 10 minutes. The results of the dissolution test are recorded in Table 12 below.

TABLE 12

| Time | % drug released in 0.1N HCl |
|---|---|
| 0 | 0 |
| 1 | 39 |
| 2 | 44 |
| 4 | 53 |
| 6 | 60 |
| 8 | 66 |
| 12 | 77 |

EXAMPLE 6

The controlled release drug delivery system was obtained as per Table 13 below—

| Ingredients | Amount in mg per tablet | % by weight of the tablet |
|---|---|---|
| Baclofen | 22.5 | 2.25 |
| mannitol | 260.0 | 26.0 |
| Hydroxyethyl cellulose (HEC 250 H) | 200 | 20.0 |
| Sodium starch glycolate | 250 | 25.0 |
| Sodium bicarbonate | 80.0 | 8.0 |
| Hydroxypropyl methylcellulose (3000-5600 mPaa) | 4.5 | 0.45 |
| Silicified microcrystalline cellulose | 90 | 9 |
| Talc | 24 | 2.4 |
| Polyethylene glycol (PEG 8000) | 10 | 1 |

-continued

| Ingredients | Amount in mg per tablet | % by weight of the tablet |
|---|---|---|
| Coat | | |
| Baclofen | 7.50 | 7.5 |
| Low viscosity Hydroxypropyl methylcellulose (4-6 mPas) | 24.0 | 2.4 |
| talc | 10.0 | 1.0 |
| Titanium dioxide | 11.0 | 1.1 |
| Propylene glycol | 5.00 | 0.5 |

The core of the gastric retention controlled drug delivery system was obtained by passing baclofen, mannitol, hydroxyethyl cellulose, sodium starch glycolate and sodium bicarbonate through ASTM (American Society for Testing and Materials) sieve #40 and mixing the ingredients to obtain a dry powder blend. An aqueous solution of HPMC K4M was then used to granulate the dry powder blend. The granules thus obtained were passed through a suitable sieve and dried. The dry granules were lubricated with a mixture of Prosolv SMCC 90, talc and PEG 8000, and compressed to obtain the cores. The cores were then coated with a hydro-alcoholic solution of a mixture of baclofen, HPMC E5, talc, propylene glycol and titanium dioxide to obtain the gastric retention controlled drug delivery system of the present invention.

The tablets thus obtained were subjected to dissolution testing at 37° C. using United States Pharmacopoeia Type II (paddle) dissolution apparatus at 50 rpm. The dissolution medium used was 1000 ml of 0.1N HCl. The tablets achieved floatation in about 6 minutes. The results of the dissolution test are recorded in Table 14 below.

TABLE 14

| | dissolution |
|---|---|
| Time | % drug released in 0.1N HCl |
| 0 | 0 |
| 1 | 55 |
| 2 | 63 |
| 4 | 75 |
| 6 | 83 |
| 8 | 91 |
| 12 | 99 |

EXAMPLE 7

The controlled release drug delivery system of the present invention was obtained as given in Table 15 below.

TABLE 15

| details of the composition | | |
|---|---|---|
| Ingredients | Quantity (mg/tab) | % by weight |
| Baclofen | 30.0 | 32.25 |
| Hydroxy ethyl cellulose (Natrosol 250 H) | 197.50 | 212.36 |
| Sodium starch glycolate | 217.50 | 233.8 |
| Microcrystalline cellulose | 435.0 | 467.74 |
| Sodium bicarbonate | 10.0 | 10.75 |
| Polyvinylpyrrolidone | 22.0 | 23.65 |
| Talc | 9.0 | 9.67 |
| Magnesium stearate | 9.0 | 9.67 |

A part of baclofen, hydroxyethylcellulose, a part of sodium starch glycolate, a part of microcrystalline cellulose and a part of polyvinylpyrrolidone, were mixed together and granulated with isopropanol and lubricated with talc and magnesium stearate to form the core granulation. The remaining parts of baclofen, microcrystalline cellulose, polyvinylpyrrolidone and sodium starch glycolate were mixed together and granulated with water to form the coat granulation. The core granulations were compressed and the coat was applied on the core using compression coating. The gastric retention controlled drug delivery system thus obtained in the form of coated tablets shows a high degree of swellability in a short time, has sufficient strength for handling as well as remaining intact in aqueous fluids, and is capable of providing a biphasic controlled release profile.

EXAMPLE 8

Comparison of morning dosing and evening dosing in single dose study in healthy volunteers. The coated capsules of Example 1 were tested for bioavailability in normal volunteers in the fed condition at different timings, that is, administration in the morning or in the evening Twenty four healthy volunteers were enrolled for the study and twenty two of them completed both the periods of the study. A randomized, open label, two treatment, two period, two sequence, single dose crossover study was carried out to assess the effect of the dosage time administration (i.e. after morning and evening administration) on the pharmacokinetics of the baclofen 60 mg extended release coated capsules of Example 1 which are suitable for once a day administration.

Figure 1:
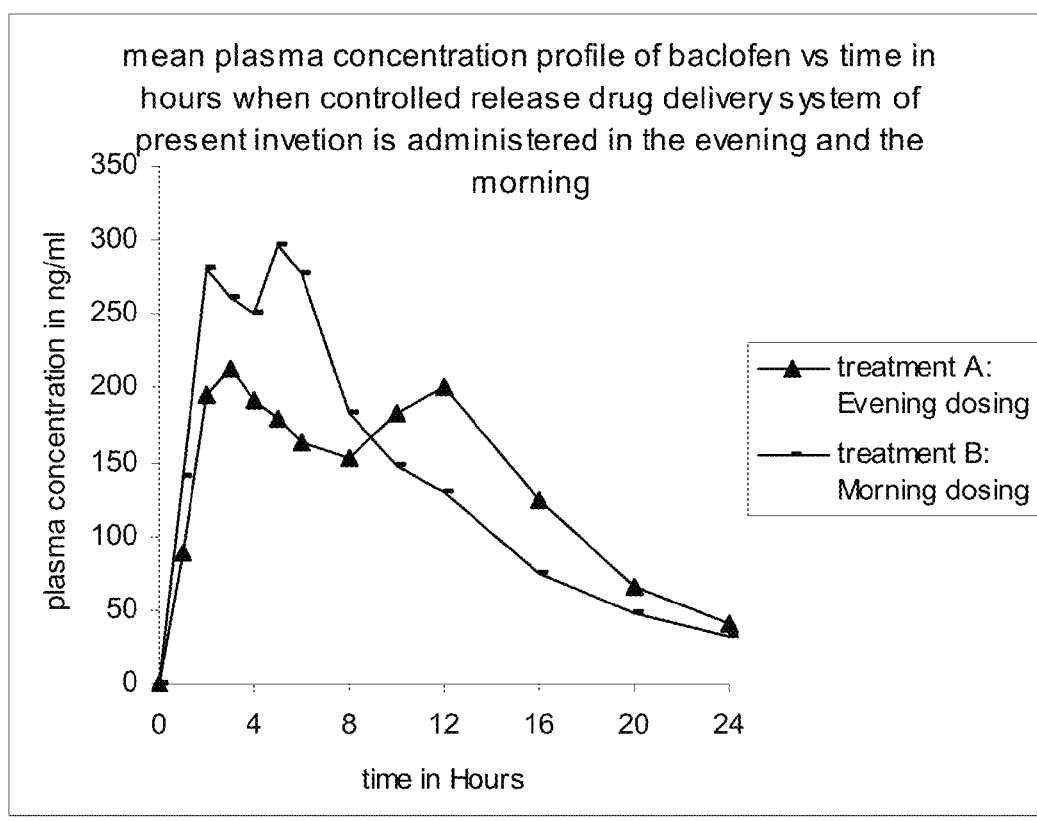
FIG. 1 depicts the mean plasma concentration profile of baclofen vs time in hours when administered in the form of a controlled release drug delivery system administered by healthy volunteers in the evening and the morning in fed condition with normal diet.

The coated capsules of Example 1 where administered by human volunteers in the evening at 7:00 pm in the fed condition. The volunteers had a normal diet for the dinner as well as morning breakfast. The human volunteers had a breakfast at 8:00 am and the dosing of the coated capsules was done at 8:30 am. The mean plasma Profile Vs time in hours in provided in Table 16 and the graph is presented in FIG. 1. The pharmacokinetic parameters that were evaluated are tabulated in Table 17.

TABLE 16

Mean plasma profile when administered by healthy volunteers in morning and evening Vs Time in hours

| Time in hours | Plasma profile achieved by administration of example 1 in the morning | Plasma profile achieved by administration of example 1 in the evening |
|---|---|---|
| 0 | 0 | 0 |
| 1 | 140.0 | 89.7 |
| 2 | 281.15 | 194.75 |
| 3 | 261.50 | 213.12 |
| 4 | 250.175 | 191.36 |
| 5 | 296.02 | 180.22 |
| 6 | 276.9 | 163.35 |
| 8 | 183.21 | 152.37 |
| 10 | 146.77 | 183.71 |
| 12 | 130.26 | 201.35 |
| 16 | 75.46 | 124.18 |
| 20 | 47.176 | 66.50 |
| 24 | 32.73 | 40.92 |

TABLE 17

Pharmacokinetic parameters

| Parameters | Study 1 (Evening Administration) | Study 2 (Morning Administration) |
|---|---|---|
| $AUC_{(0-t)}$ (ng · hr · ml −1) | 3432.4552 (% CV = 22.5) | 3402.6867 (% CV = 19.9) |
| $AUC_{(0-\infty)}$ (ng · hr · ml −1) | 3541.8082 (% CV = 22.8) | 3476.8758 (% CV = 20.2) |
| Ln $C_{max}$ (ng · ml −1) | 253.239 (% CV = 23.4) | 346.714 (% CV = 22.6) |
| $T_{max}$ (hr) | 8.0 (% CV = 60.6) | 5.0 (% CV = 48.2) |

EXAMPLE 9

A simulation was done with single dose data (twenty two subjects) of dosage time effect (i.e. after morning and evening administration). Pharmacokinetic study on Baclofen 60 mg as described in Example 1 were performed by using method of Nonparametric superposition in WinNonlin 5.0 of Pharsight Corporation, USA. Software used for performing simulation: WinNonlin (version 5.0) of Pharsight Corporation, USA. The method used for performing simulation was Non-parametric superposition method. Non-parametric superposition function is used to predict drug concentrations after multiple dosing at steady state, and is based on non-compartmental results describing single dose data. The predictions are based upon an accumulation ratio computed from the elimination rate constant. PK Sampling points considered for simulation were 0.0 (Pre-dose), 1.0, 2.0, 3.0, 4.0, 5.0, 6.0, 8.0, 10.0, 12.0, 16.0, 20.0, 24.0, 30.0 and 36.0 hours. Data of both morning & Evening dose have been simulated for 7 consecutive days and dosing interval of 24 hr (once daily dose) has been considered. The mean plasma concentration profile is presented in table 18 and FIG. 3. The steady state data results are reported in Table 19 and 20 below.

TABLE 18

Mean plasma concentration Vs time in hours

| Time in hours | Plasma profile achieved by administration of example 1 in the morning | Plasma profile achieved by administration of example 1 in the evening |
|---|---|---|
| 0 | 35.561 | 44.610 |
| 1 | 172.5 | 130.7 |
| 2 | 310.6 | 232.2 |
| 3 | 287.875 | 247.067 |
| 4 | 273.53 | 221.8 |
| 5 | 316.4 | 207.2 |
| 6 | 294.3 | 186.9 |
| 10 | 158.6 | 200.16 |
| 12 | 139.4 | 214.35 |
| 16 | 81.3 | 132.6 |
| 20 | 50.9 | 72.1 |
| 24 | 35.6 | 44.61 |

TABLE 19

Summary of statistical evaluation of simulated baclofen steady state data (n = 22)

| Parameters | | System according to example 1 administered in the evening (PM) (Treatment A) | System according to example 1 administered in the morning (AM) (Treatment B) |
|---|---|---|---|
| | | Mean ± SD | |
| $AUC_{0-24}$ | (ng·h/mL) | 3637.5346 ± 830.61288 | 3550.6908 ± 715.23662 |
| $C_{max}$ | (ng/mL) | 282.517 ± 61.5016 | 377.449 ± 78.1262 |
| $C_{min}$ | (ng/mL) | 44.610 ± 17.2971 | 35.561 ± 17.6041 |
| $T_{max}$ | (h) | 6.818 | 4.682 |
| $T_{max}$* | (h) | 5.00 | 5.00 |
| Fluctuation | (%) | 160.128 ± 32.4217 | 236.634 ± 55.6358 |
| $T_{1/2}$ | (h) | 5.2801 ± 0.77668 | 6.3479 ± 1.38080 |

*Median value

The data tabulated in Tables 19 indicates that when the claimed controlled release drug delivery system was administered every 24 hours as an evening dose of baclofen for consecutively 7 days (simulated data using software) wherein the plasma levels at steady state (for 7 days) shows lesser peak plasma concentration compared to the peak plasma concentration achieved at a steady state level as compared to the plasma levels achieved after morning dosing. FIG. 3 indicates a much flattened plasma baclofen concentration time profiles after evening dosing compared to the morning dosing.

EXAMPLE 10

A randomized, open-label, two-treatment, two-period, two-sequence, multiple dose, crossover study to assess bioavailability and steady State pharmacokinetics of baclofen 30 mg controlled release drug delivery system of the present invention was given once daily, under fed (normal meal) conditions in the morning time, for 8 consecutive days in patients suffering from spasticity. Baclofen 10 mg immediate release tablets were given three times a day at 8 hour interval, with the initial dose administered under fasting condition, for 8 consecutive days, in 24 Spastic subjects receiving stable daily doses of baclofen.

The pharmacokinetic results in terms of bioavailability, i.e $C_{max}$, $T_{max}$ and AUC were recorded which were in comparison with the equivalent dose of immediate release baclofen that was administered three times a day (Reference=R).

TABLE 20

Mean plasma concentration Vs time in hours when controlled drug delivery system is administered in morning

| Time in hours on 8 day (168 hours) | Plasma profile achieved by administration of 30 mg baclofen controlled drug delivery system of present invention by spastic patients in the morning | Plasma profile achieved by administration of 10 mg baclofen immediate release tablets administered by spastic patients three times a day |
|---|---|---|
| 0 | 63.97 | 111.85 |
| 1 | 148.83 | 247.52 |
| 2 | 209.79 | 241.27 |
| 3 | 201.54 | 204.27 |
| 4 | 203.02 | 166.41 |
| 5 | 211.91 | — |
| 6 | 210.27 | — |
| 8 | 184.1 | 99.5 |
| 10 | 157.3 | 172.9 |
| 11 | — | 172.46 |
| 12 | 140.87 | — |
| 16 | 102.34 | 119.14 |
| 20 | 73.79 | 178.74 |
| 24 | 50.27 | 107.50 |

TABLE 21

Summary of the pharmacokinetic parameters obtained on once-a-day administration of baclofen controlled release drug delivery system in morning Vs immediate release baclofen tablets three times a day (number of patients = 11)

| | Least square means | | | | |
|---|---|---|---|---|---|
| PK variables | Controlled release drug delivery system 30 mg baclofen (A) | Immediate Release baclofen tablets (B) | Ratio of A/B | % CV | 90% confidence interval |
| $AUC_{(0-\infty)}$ | 3027.44 | 3555.03 | 85.16 | 16.53 | 74.52-97.31 |
| $C_{max}$ | 242.26 | 254.04 | 95.36 | 17.88 | 82.56-110.15 |
| $T_{max}$ | 5 | 2 | | 11 | |

EXAMPLE 11

A randomized, open-label, two-treatment, two-period, two-sequence, multiple dose, crossover study to assess bioavailability and steady State pharmacokinetics of baclofen 30 mg controlled release drug delivery system of the present invention was given once daily in the evening time, under fed (normal meal) conditions, for 8 consecutive days in patients suffering from spasticity. Baclofen 10 mg immediate release tablets were given three times a day at 8 hour interval, with the initial dose administered under fasting condition, for 8 consecutive days, in 24 Spastic subjects receiving stable daily doses of baclofen.

The pharmacokinetic results in terms of bioavailability, i.e $C_{max}$, $T_{max}$ and AUC were recorded which were in comparison with the equivalent dose of immediate release baclofen that was administered three times a day (Reference=R).

TABLE 22

Mean plasma concentration Vs time in hours when controlled drug delivery system is administered in the evening

| Time in hours on 8 day (168 hours) | Plasma profile achieved by administration of 30 mg baclofen controlled drug delivery system by spastic patients in the evening | Plasma profile achieved by administration of 10 mg baclofen immediate release tablets administered by spastic patients three times a day |
|---|---|---|
| 0 | 55.77 | 120.92 |
| 1 | 99.55 | 312.48 |
| 2 | 162.24 | 277.37 |
| 3 | 197.24 | 224.54 |
| 4 | 205.98 | 190.125 |

TABLE 22-continued

Mean plasma concentration Vs time in hours when controlled drug delivery system is administered in the evening

| Time in hours on 8 day (168 hours) | Plasma profile achieved by administration of 30 mg baclofen controlled drug delivery system by spastic patients in the evening | Plasma profile achieved by administration of 10 mg baclofen immediate release tablets administered by spastic patients three times a day |
|---|---|---|
| 5 | 205.08 | — |
| 6 | 191.50 | — |
| 8 | 265.33 | 103.45 |
| 10 | 236.59 | 152.40 |
| 11 | — | 191.60 |
| 12 | 198.26 | 197.01 |
| 16 | 117.19 | 103.51 |
| 18 | — | 202.33 |
| 20 | 73.05 | — |
| 24 | 43.94 | 111.21 |

TABLE 23

Summary of the pharmacokinetic parameters obtained on once-a-day administration of baclofen controlled release drug delivery system in evening Vs immediate release baclofen tablets three times a day. (number of patients = 12)

| | Least square means | | | | |
|---|---|---|---|---|---|
| PK variables | Controlled release drug delivery system 30 mg baclofen (A) | Immediate Release baclofen tablets (B) | Ratio of A/B | % CV | 90% C.I |
| $AUC_{(0-\infty)}$ | 3431.56 | 3947.06 | 86.94 | 12.78 | 79.12-95.53 |
| $C_{max}$ | 286.71 | 304.83 | 94.05 | 22.35 | 79.87-110.75 |
| $T_{max}$ | 8 | 1 | | | |

The values indicate that the bioavailability achieved when the baclofen controlled release drug delivery system prepared similar to example 1 in the spastic patients in comparison to the equivalent dose of immediate release baclofen tablets, when administered in the evening on fed condition in comparison to the bioavailability achieved when the baclofen controlled release capsules as per example 1 when administered in the morning. The $T_{max}$ was prolonged when the same composition was administered in the evening in comparison to the morning. The T/R ratio of the AUC i.e extent of absorption was found to be better when the controlled release system was administered in the evening in comparison to the administration in the morning. The rate of absorption was better when the controlled release system was administered in the evening in comparison to the morning.

Prophetic examples of controlled release drug delivery systems are provided below. It should be understood that the constituents and/or proportions of the constituents in these coatings as well as the amounts thereof may be varied in order to achieve formulations possessing different release characteristics. In all instances wherein prophetic examples are provided these compositions are intended to be exemplary and it should be understood that the specific procedures, constituents, amounts thereof and the like may be varied in order to obtain a composition possessing desired properties.

PROPHETIC EXAMPLES

EXAMPLE 12

TABLE 24

Details of the controlled release drug delivery system

| Sr. No. | Ingredients | Mg per capsule | Percent by weight |
|---|---|---|---|
| | Sustained release granules | | |
| 1. | Baclofen | 22.5 | 14.5 |
| 2. | Mannitol | 80.4 | 60.5 |
| 3. | Starch | 65 | 21.8 |
| 4. | Dimethylamino ethyl methacrylate with neutral methacrylate esters | 20 | 10 |
| 5. | Talc | 3 | 1.5 |
| 6. | Magnesium stearate | 2 | 1.0 |
| | Immediate release coating | | |
| 6. | Baclofen | 7.5 | 13.0 |
| 7. | Hydroxypropyl methylcellulose (4-6 mPas) | 24.0 | 41.7 |
| 8. | Talc | 10.0 | 17.4 |
| 9. | Propylene glycol | 5.0 | 8.7 |
| 10. | Titanium dioxide | 11.0 | 19.1 |
| 11. | Purified Water USP | q.s | |

Baclofen is mixed with mannitol, starch and talc. The mixture is granulated with solution of dimethylamino ethyl methacrylate with neutral methacrylate esters. The granules are lubricated with talc and are filled into hard gelatin capsules. The capsule is further coated with a solution of immediate release fraction of baclofen which is dispersed in a film coating solution of low viscosity hydroxypropyl methylcellulose.

EXAMPLE 13

TABLE 25

Details of the controlled release drug delivery system

| Sr. No. | Ingredients | mg per capsule | Percent by weight |
|---|---|---|---|
| 1 | Baclofen | 35 | 70 |
| 2 | Ethyl cellulose | 7.5 | 15 |
| 3 | Microcrystalline cellulose | 4.25 | 8.5 |
| 4 | Croscarmellose sodium | 0.25 | 0.5 |
| 5 | Ethyl alcohol | q.s | q.s |
| 6 | Purified water | q.s | q.s |

Specified amounts of Baclofen may be taken and mixed with specified amounts of microcrystalline cellulose and Croscarmellose sodium. The blend is uniformly mixed and the powder blend is granulated with a polymeric hydro-alcoholic solution of ethyl-cellulose in a fluidized bed granulator. The granules so formed are further coated with hydro-alcoholic solution of ethyl-cellulose. These coated granules represent a reservoir type of controlled drug delivery system wherein the release of baclofen is controlled by the matrix as well the reservoir mechanism. The coated granules may be filled into hard gelatin capsules or may be compressed into tablets of size of about 2 millimeter (2 mm) and then filled into hard gelatin capsules.

EXAMPLE 14

TABLE 26a

Details of the controlled release drug delivery system in the form of bilayer coated compressed tablet

| Ingredients | mg per tablet | Percent by weight of the drug delivery system |
|---|---|---|
| Composition of the First Layer | | |
| Baclofen | 35 | 11.25 |
| Hydroxypropyl methylcellulose (12,000 to 21000 mPas) | 20.00 | 10.0 |
| Lactose anhydrous | 88.50 | 44.25 |
| Polyvinylpyrrolidone | 6.5 | 3.25 |
| Colloidal silicon dioxide | 2.0 | 1.00 |
| Stearic acid | 2.0 | 3.00 |
| Talc | 4.00 | 1.00 |
| Composition of the second Layer | | |
| Baclofen | 25 mg | 25 |
| Silicified microcrystalline cellulose | 205.0 | 70.7 |
| Crospovidone | 72.5 | 25.0 |
| Colloidal silicon dioxide | 7.2 | 2.5 |
| Sodium lauryl sulfate | 2.90 | 1.0 |
| Magnesium stearate | 2.4 | 0.83 |

TABLE 26 b

Functional coating composition

| Ingredients | mg per core tablet of the core | Percent w/w dry weight 8% weight gain |
|---|---|---|
| Functional coating of water insoluble polymeric coating of ethylcellulose commercially available as Aquacoat EC30 D* | 77.52 | 8 |
| Ethyl cellulose | 20.93 | 69.21 |
| Sodium lauryl sulphate | 0.7752 | 2.56 |
| Cetyl alcohol | 1.55 | 5.12 |
| Dibutyl sebacate | 5.81 | 19.21 |
| Triethyl citrate | 1.16 | 3.83 |
| water | q.s | q.s |

Controlled release drug delivery system of baclofen of the present invention may be obtained in the form of a bilayer tablet that is functionally coated. Portion of baclofen is incorporated in the second layer for the immediate release and portion of baclofen is incorporated in the first layer for the controlled release.

Composition of First Controlled Release Layer:

Specified amounts of baclofen, Hydroxypropyl methylcellulose (12,000 to 21000 mPas), lactose anhydrous, polyvinyl pyrrolidone and colloidal silicon dioxide are sieved and mixed thoroughly. Stearic acid and talc are sieved and mixed with the blend, to obtain the composition of the first layer.

Composition of the Second Layer:

For the immediate release fraction, baclofen, silicified microcrystalline cellulose, colloidal silicon dioxide, sodium lauryl sulfate and crospovidone were sieved and mixed thoroughly to obtain a blend. This blend was lubricated with magnesium stearate, to obtain the composition of the second layer. The two compositions were compressed using standard concave punches to obtain bilayer tablets. The compressed tablets were coated with the coating composition to a weight gain of about 8% by weight of the core. An orifice of size of about 500 microns was drilled on the side of the tablet that contained the second layer.

EXAMPLE 15

TABLE 27

Drug loading on non-pareil seeds

| Ingredients | mg per dosage form | % by weight of the dosage from |
|---|---|---|
| Non-pareil seeds (NPS) | 81.4 | 81.4 |
| Baclofen | 13.0 | 13.0 |
| Hypromellose, Methocel E | 5.6 | 5.6 |
| Purified Water, USP | q.s | q.s |
| Functional coating | | |
| Ethylcellulose | 8.5 | 8.5 |
| Hydroxy propyl methylcellulose | 2.12 | 2.12 |
| Purified Water, USP | q.s | q.s |

The non-pareil seeds are loaded with a baclofen suspended in specified amounts of hypromellose in purified water. The loaded non-pareil seeds are then functionally coated with ethyl cellulose in a fluidized bed coating apparatus. The weight gain of the functional coating can range from about 10-20% by weight of the non-pareil seeds. The functionally coated pellets may be further coated with an immediate release fraction of baclofen to achieve an immediate release of baclofen followed by controlled release of the baclofen. The details are given in the following table 27a.

TABLE 27 a

Immediate release coating
Immediate release coating

| | | | |
|---|---|---|---|
| 1 | Baclofen | 7.5 | 13.0 |
| 2 | Hydroxypropyl methylcellulose (4-6 mPas) | 24.0 | 41.7 |
| 3 | Talc | 10.0 | 17.4 |
| 4 | Propylene glycol | 5.0 | 8.7 |
| | Titanium dioxide | 11.0 | 19.1 |
| 6 | Purified Water USP | q.s | |

EXAMPLE 16

TABLE 28

Compressed dosage form of baclofen having a muco-adhesive polymer in matrix

| Ingredients | mg per tablet | Percent by weight of the controlled release drug delivery system |
|---|---|---|
| Baclofen | 5 | 10 |
| Polyethylene oxide | 3.5 | 7 |
| Sodium carboxy methyl-cellulose | 1.5 | 3 |
| Lactose anhydrous | 10 | 20 |
| Microcrystalline cellulose | 25.9 | 51.8 |
| Polyvinyl pyrrolidone | 2.5 | 5 |
| Colloidal silica | 0.05 | 0.1 |
| Purified talc | 0.05 | 0.1 |
| Magnesium stearate | 0.5 | 1.0 |

Specified quantities of baclofen are mixed geometrically with polyethylene oxide, sodium carboxymethylcellulose, lactose anhydrous and microcrystalline cellulose. The mixture is sifted and blended in a double polyethene bag till a uniform mixture is obtained. The blend is granulated with a binding solution of polyvinyl pyrrolidone in isopropyl alcohol. The dried granules are lubricated with colloidal silicon dioxide, purified talc and magnesium stearate by mixing for 2 minutes. The mini tablets have a diameter of about 1.5 mm and a length of about 2 mm.

EXAMPLE 17

TABLE 29

Microparticulate dosage form of baclofen having a muco-adhesive polymer coating

| Ingredients | mg per dosage form | Percent by weight of the controlled release drug delivery system |
|---|---|---|
| Baclofen | 12.5 | 25 |
| Ethyl cellulose | 3.3 | 6.6 |
| magnesium stearate | 0.4 | 0.89 |
| Castor oil | 0.4 | 0.72 |
| Polyvinyl pyrrolidone | 0.4 | 0.72 |
| Polyethylene oxide | 25.0 | 50 |
| Hydroxypropyl methyl cellulose (80,000-1,20,000 mPas) | 6.6 | 13.12 |
| Calcium acetate | 0.8 | 1.57 |

Specified amounts of baclofen are loaded in a fluid bed chamber. A coating solution of ethyl cellulose, polyvinyl pyrrolidone, castor oil and lubricant is prepared by dissolving the ingredients in isopropyl alcohol. Baclofen is then film coated with this coating solution. These film-coated baclofen microparticles particles are subsequently dry blended in a cube mixer with a mixture of sodium alginate powder, hydroxypropylmethylcellulose powder and calcium acetate powder. This mixture is filled in hard gelatin capsules.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method of treating spasticity; said method comprising orally administering once-a-day in the evening a gastric retention controlled release drug delivery system comprising baclofen or its pharmaceutically acceptable salt and pharmaceutically acceptable excipients wherein the gastric retention controlled release drug delivery system comprises a first composition, a second composition and a third composition, wherein the first composition comprises an immediately releasing fraction of the baclofen dose and surrounds the third composition;

the second composition comprises a first region comprising a slow release fraction of the total dose of baclofen present in the gastric retention controlled release drug delivery system and excipients filled into hard gelatin capsule, and a second region which is a sub-coating applied on the filled hard gelatin capsule and the second region comprises swellable polymers, gas generating agent and superdisintegrants and does not contain baclofen further wherein at least one swellable polymer is a polymer obtained by polymerization of the monomers, butyl methacrylate, 2-dimethyl aminoethyl methacrylate and methyl methacrylate and is soluble below about pH 5 and swellable and permeable above pH 5;

the third composition comprises methacrylic acid copolymer Type C, polycarbophil, gas generating agent and superdisintegrants and mixtures thereof.

2. A method as claimed in claim 1, wherein the gastric retention controlled release drug delivery system comprises baclofen or its pharmaceutically acceptable salt in amounts from equivalent to 5 mg to 80 mg of baclofen and pharmaceutically acceptable excipients.

3. A method as claimed in claim 1, wherein the method provides a bi-modal plasma concentration time profile.

4. A method as claimed in claim 3, wherein the bi-modal plasma concentration time profile is such that the first plasma peak is obtained at an earlier time between 2 hours to 8 hours and the second peak is obtained at a time between 8 hours to 18 hours.

5. A method as claimed in claim 4, wherein the bi-modal plasma concentration time profile is such that the first plasma peak is obtained at an earlier time between 2 hours to 4 hours and the second peak is obtained at a time between 10 hours to 14 hours.

6. A method as claimed in claim 1, wherein the swelling index of the gastric retention controlled release drug delivery system at 6 hours upon contact with an aqueous environment is from about 5 to about 15.

7. A method as claimed in claim 1, wherein the ratio of the fraction of total dose of baclofen present in the first composition to the second composition ranges from about 1:1 to 1:3.

8. A method as claimed in claim 1, wherein the ratio of the fraction of total dose of baclofen present in the first composition to the second composition ranges from about 1:1 to 1:1.5.

9. A method as claimed in claim 1, wherein the swelling index of capsules of the gastric retention controlled release drug delivery system at 6 hours upon contact with an aqueous environment is from about 6 to about 12.

10. A method as claimed in claim 1, wherein the excipient selected from the group consisting of swellable polymers, gas generating agents, superdisintegrants and mixtures thereof is also present in the first region.

11. A method as claimed in claim 1, wherein the second composition comprises a hydrophobic material selected from the group consisting of waxes, oils, fatty acid and mixtures thereof.

12. A method as claimed in claim 1, wherein the second composition comprises water soluble materials.

* * * * *